US011849031B2

(12) United States Patent
Carver et al.

(10) Patent No.: US 11,849,031 B2
(45) **Date of Patent: *Dec. 19, 2023**

(54) METHOD AND SYSTEM FOR DIGITAL HEALTH DATA ENCRYPTION

(71) Applicant: OrangeDot, Inc., Santa Monica, CA (US)

(72) Inventors: Joshua Carver, Santa Monica, CA (US); Puneet Thapliyal, Santa Monica, CA (US); Alex Boisvert, Santa Monica, CA (US)

(73) Assignee: OrangeDot, Inc., Santa Monica, CA (US)

( * ) Notice: Subject to any disclaimer, the term of this patent is extended or adjusted under 35 U.S.C. 154(b) by 1 day.

This patent is subject to a terminal disclaimer.

(21) Appl. No.: 17/833,056

(22) Filed: Jun. 6, 2022

(65) Prior Publication Data

US 2022/0303126 A1 Sep. 22, 2022

Related U.S. Application Data

(63) Continuation of application No. 17/401,956, filed on Aug. 13, 2021, now Pat. No. 11,387,987.

(60) Provisional application No. 63/065,271, filed on Aug. 13, 2020.

(51) Int. Cl.

| | |
|---|---|
| ***H04L 9/08*** | (2006.01) |
| ***G06F 21/62*** | (2013.01) |
| ***G16H 80/00*** | (2018.01) |
| ***H04L 9/14*** | (2006.01) |
| ***H04L 9/30*** | (2006.01) |

(52) U.S. Cl.

CPC ........ *H04L 9/0833* (2013.01); *G06F 21/6254* (2013.01); *G16H 80/00* (2018.01); *H04L 9/14* (2013.01); *H04L 9/3073* (2013.01)

(58) Field of Classification Search

CPC ....... H04L 9/0833; H04L 9/14; H04L 9/3073; G16H 80/00; G06F 21/6254

See application file for complete search history.

(56) References Cited

U.S. PATENT DOCUMENTS

| | | | |
|---|---|---|---|
| 7,587,368 B2 | 9/2009 | Felsher | |
| 2003/0033168 A1 | 2/2003 | Califano et al. | |
| 2004/0059599 A1 | 3/2004 | McIvor | |
| 2007/0006322 A1* | 1/2007 | Karimzadeh | G06F 21/6227 726/28 |
| 2008/0021834 A1 | 1/2008 | Holla et al. | |
| 2010/0246827 A1 | 9/2010 | Lauter et al. | |

(Continued)

OTHER PUBLICATIONS

"Mobile device administration for secure and manageable health data collection in under-resourced areas", ACM (Year 2016).

(Continued)

*Primary Examiner* — Shanto Abedin

(74) *Attorney, Agent, or Firm* — Jeffrey Schox; Caitlin Ploch

(57) ABSTRACT

A system for data encryption includes any or all of: a set of items, a set of keys, and a server. A method for data encryption includes any or all of: encrypting items, sharing items, and reading items. The method can optionally additionally or alternatively include any or all of: performing a registration process, creating items, restricting access of users and/or supplementary systems to items, and/or any other suitable processes.

14 Claims, 13 Drawing Sheets

(56) References Cited

U.S. PATENT DOCUMENTS

| | | | |
|---|---|---|---|
| 2011/0066863 A1 | 3/2011 | Katzenbeisser et al. | |
| 2013/0054467 A1 | 2/2013 | Dala et al. | |
| 2014/0164784 A1* | 6/2014 | Sinderbrand | G06F 21/602 713/189 |
| 2016/0275309 A1* | 9/2016 | Austin | G06F 21/6254 |
| 2016/0277374 A1* | 9/2016 | Reid | H04L 63/0435 |
| 2018/0063104 A1 | 3/2018 | Manges | |
| 2019/0362083 A1 | 11/2019 | Ortiz et al. | |
| 2020/0195621 A1* | 6/2020 | Li | H04L 9/0822 |
| 2021/0075623 A1 | 3/2021 | Petersen | |

OTHER PUBLICATIONS

Ohr, Hans , et al., “Securing the E-health cloud”, ACM (Year: 2010).
Malin, Bradley , et al., “A Secure Protocol to Distribute Unlinkable Health Data”, AMIA Symposium Proceedings. (Year: 2005).
Zheng, Xiaochen , et al., “Blockchain-based Personal Health Data Sharing System Using Cloud Storage”, IEEE. (Year: 2018).

* cited by examiner

METHOD AND SYSTEM FOR DIGITAL HEALTH DATA ENCRYPTION

CROSS-REFERENCE TO RELATED APPLICATIONS

This application is a continuation of U.S. application Ser. No. 17/401,956, filed 13 Aug. 2021, which claims the benefit of U.S. Provisional Application No. 63/065,271, filed 13 Aug. 2020, each of which is incorporated in its entirety by this reference.

TECHNICAL FIELD

This invention relates generally to the digital health field, and more specifically to a new and useful system and method for data encryption in the digital health field.

BACKGROUND

Current software systems and platforms, especially in digital health, can involve a wide variety of sensitive data. Mass data leaks are consequently a significant concern and a potentially huge problem. Conventional systems and methods typically implement end-to-end encryption as protection against this, but typically only for limited data formats such as cloud-based password managers and encrypted chats. And for those which do handle varied datasets (e.g., without end-to-end encryption), these systems and methods are often vulnerable to mass data leaks, in which a breach of security can result in a hacker having access to large amounts—if not all—of the stored data.

Thus, there is a need in the digital health field to create an improved and useful system and method for robustly protecting a wide variety of sensitive data.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
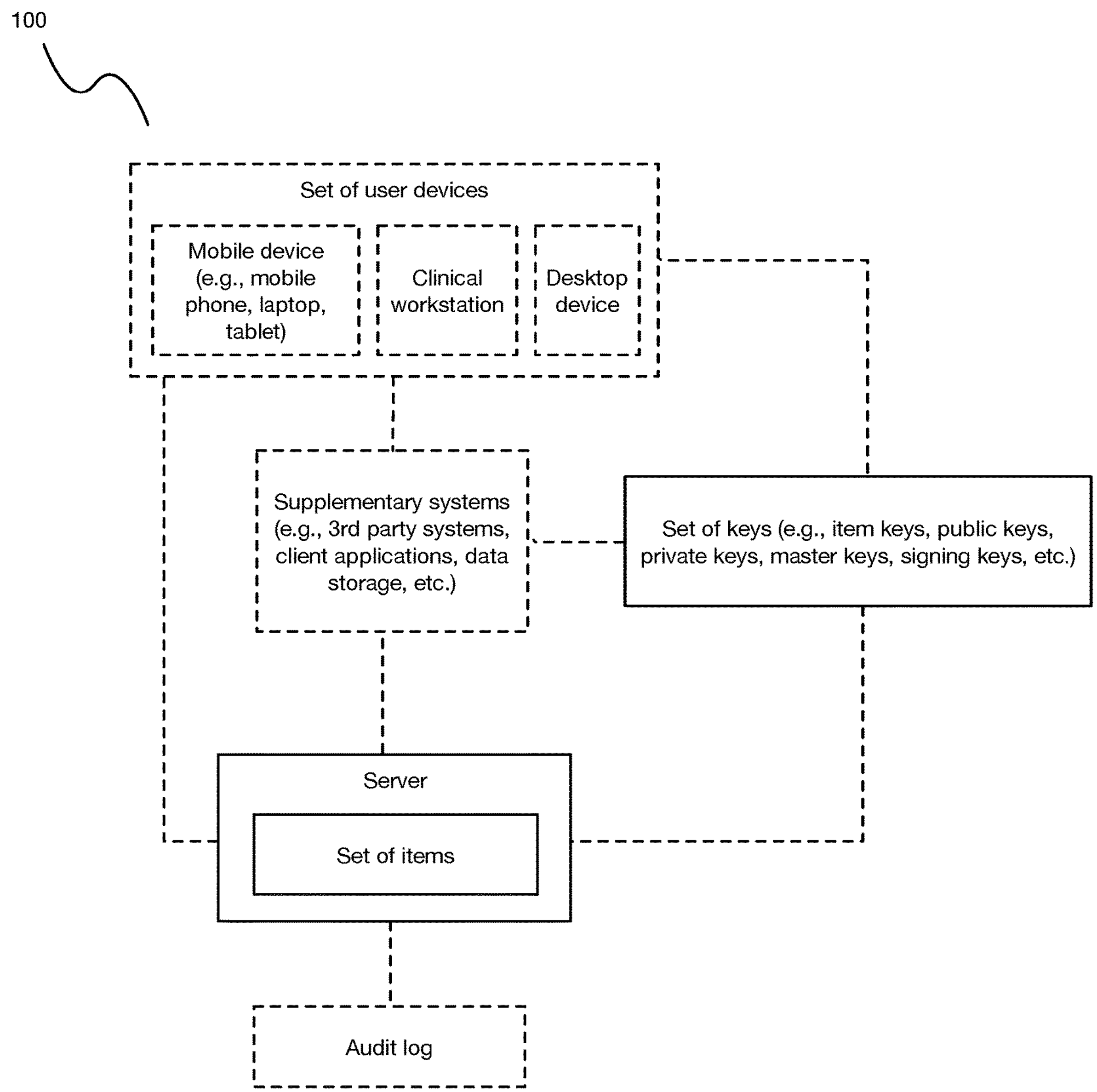
FIG. 1 is a schematic of a system for digital health data encryption.

As shown in FIG. 1, a system 100 for data encryption and/or sharing includes and/or interfaces with: a set of items, a set of keys, and a server (equivalently referred to herein as the vault and/or the vault server and/or the first server). The system 100 can optionally additionally include and/or interface with any or all of: one or more client applications, one or more application programming interface (API) layers, a set of user devices and/or other supplementary systems, and/or any other components. Additionally or alternatively, the system 100 can include and/or interface with a second server or any number of other servers, and/or any other suitable components or combination of components.

The system 100 can additionally or alternatively include and/or interface with any or all of the systems, components, embodiments, and/or examples as described in any or all of: U.S. application Ser. No. 13/969,349, filed 16 Aug. 2013; U.S. application Ser. No. 14/839,232, filed 28 Aug. 2015; U.S. application Ser. No. 15/005,923, filed 25 Jan. 2016; U.S. application Ser. No. 15/069,163, filed 14 Mar. 2016; U.S. application Ser. No. 15/265,454, filed 14 Sep. 2016; U.S. application Ser. No. 15/482,995, filed 10 Apr. 2017; and U.S. application Ser. No. 15/587,599, filed 5 May 2017; each of which is incorporated herein in its entirety by this reference.

Figure 2:
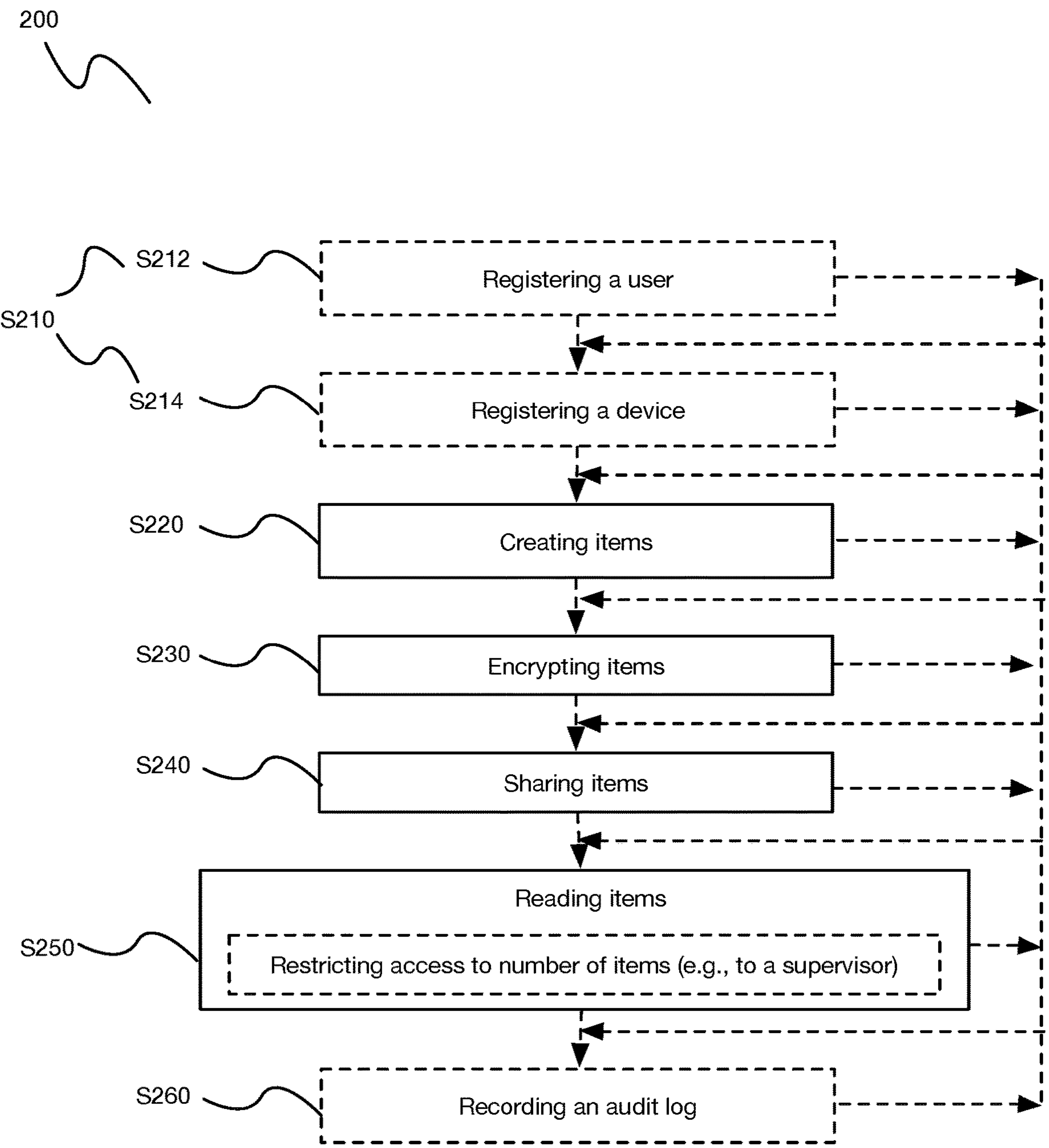
FIG. 2 is a schematic of a method for digital health data encryption.

As shown in FIG. 2, a method 200 for data encryption and/or sharing includes any or all of: encrypting items S230, sharing items S240, and reading items S250. The method 200 can optionally additionally or alternatively include any or all of: performing a registration process S210, creating items S220, restricting access of users and/or supplementary systems to items, and/or any other suitable processes. Any or all of these processes can be individually performed, performed together (e.g., creating items can include encrypting items), or performed in any suitable combination. The method 200 is preferably performed with a system 100 as described above, but can additionally or alternatively be performed with any other suitable system(s).

The method 200 can additionally or alternatively include and/or interface with any or all of the methods, processes, embodiments, and/or examples as described in any or all of: U.S. application Ser. No. 13/969,349, filed 16 Aug. 2013; U.S. application Ser. No. 14/839,232, filed 28 Aug. 2015; U.S. application Ser. No. 15/005,923, filed 25 Jan. 2016; U.S. application Ser. No. 15/069,163, filed 14 Mar. 2016; U.S. application Ser. No. 15/265,454, filed 14 Sep. 2016; U.S. application Ser. No. 15/482,995, filed 10 Apr. 2017; and U.S. application Ser. No. 15/587,599, filed 5 May 2017; each of which is incorporated herein in its entirety by this reference.

2. Benefits

The system and method for digital health data encryption can confer several benefits over current systems and methods.

In a first variation, the system and/or method confers the benefit of enabling encryption and selective sharing of diverse types and/or sizes of data, and particularly sensitive data, such as medical records, sensor data, and large files like video (e.g., telehealth appointments). In specific examples, for instance, the system and/or method enables the encryption and selective sharing of all types data involved in a digital health platform, such as, but not limited to: video files (e.g., video messages, video course materials for a digital health program, video tele-therapy appointments between participants of the program and clinicians and/or coaches, from video conferences between participants and coaches, from video conferences between coaches, other video conferences, etc.), text files of various formats (e.g., from messages, reports, surveys, notes, etc.), audio files, and/or any other file types.

In a second variation, additional or alternative to the first, the system and/or method confers the benefit of enabling secure, complex sharing of data between any or all of: different users, users and systems, different systems, and/or any other entities. The system and/or method further preferably confers the benefit of enabling selective sharing of this data, such that users and systems are only able to access data which is specifically shared with them. In specific examples, the system and/or method enables the secure sharing of sensitive data (e.g., health information, clinical information, personal information, sensitive communications, etc.) with selective people (e.g., clinicians, health coaches, etc.) and/or systems.

In a third variation, additional or alternative to those described above, the system and/or method confers the benefit of enabling the identification and sharing of only a portion of the fields of a record.

In a fourth variation, additional or alternative to those described above, the system and/or method confers the benefit of creating and maintaining a robust and trustworthy audit log (e.g., a cryptographic audit log), such as an audit log with strong cryptographic guarantees. In specific examples, this can function as a deterrent to users who have access to the system 100 from abusing it. For mental health companies, for instance, a coach supervisor may have access to a significant amount of data but is not supposed to access it on a whim (e.g., at random times, in large amounts, etc.); an audit log can serve as a deterrent from doing this as well as enable notice/evidence that such an event has happened. Additionally or alternatively, the audit log can function to maintain a robust tracking of items and associated actions (e.g., views, sharing, etc.), a robust tracking of user activity (e.g., what information users are accessing, which users are the most active, which users are the least active, etc.), and/or any other information. The audit log can further additionally or alternatively function to enable various measures (e.g., triggers) to be put in place based on this information, such as an alert in an event that a single user accesses data in an amount and/or frequency greater than a predetermined threshold.

In a fifth variation, additional or alternative to those described above, the system and/or method confers the benefit of protecting sensitive data and preventing massive data breaches by distributing keys among different locations, such as keeping one or more keys outside of the server and/or other components of the system 100 (e.g., so an attacker cannot break in to the server and gain access to everything, such that an Insecure Direct Object Reference [IDOR] breach is prevented, etc.). In specific examples, encrypted versions of each users' public and private encryption keys are stored at and/or otherwise accessible by the server, along with unencrypted public keys, whereas the master encryption keys used to decrypt the encryption key-pair are held by the users outside of the server. In additional or alternative specific examples, the system and/or method function to keep large amounts of sensitive data outside of areas which are conventionally compromised in attacks (e.g., API layers, databases, etc.) and instead distribute it among users. As such, an attacker would essentially have to compromise every single user individually in order to access all of the data. Additionally or alternatively, keys can be otherwise held and/or distributed.

In a sixth variation, additional or alternative to those described above, the system and/or method confers the benefit of enabling data to be encrypted and selectively shared without using blockchain technologies, which can enable the system and method described herein to be any or all of: more efficient, more secure, more scalable, and/or have any other advantages over blockchain technologies. Alternatively, any or all of the system and/or method can include and/or interface with blockchain technologies.

In a seventh variation, additional or alternative to those described above, the system and/or method confers the benefit of including and/or interfacing with multiple servers, wherein the users interact with a first server storing the encrypted items, and wherein a second server is not accessible by the users and includes un-encrypted (e.g., plaintext) items for regulatory and/or compliance purposes (and/or for data scientists to access in a controlled and limited fashion for algorithm/model development). Additionally or alternatively, any other number of servers can be implemented.

Additionally or alternatively, the system and method can confer any other benefit.

3. System

As shown in FIG. 1, the system 100 includes and/or interfaces with: a set of items, a set of keys, and a server (equivalently referred to herein as the vault and/or the vault server and/or the first server). The system 100 can optionally additionally include and/or interface with any or all of: one or more client applications, one or more application programming interface (API) layers, a set of user devices and/or other supplementary systems, and/or any other components. Additionally or alternatively, the system 100 can include and/or interface with a second server or any number of other servers, and/or any other suitable components or combination of components.

The system 100 can additionally or alternatively include and/or interface with any or all of the systems, components, embodiments, and/or examples as described in any or all of: U.S. application Ser. No. 13/969,349, filed 16 Aug. 2013; U.S. application Ser. No. 14/839,232, filed 28 Aug. 2015; U.S. application Ser. No. 15/005,923, filed 25 Jan. 2016; U.S. application Ser. No. 15/069,163, filed 14 Mar. 2016; U.S. application Ser. No. 15/265,454, filed 14 Sep. 2016; U.S. application Ser. No. 15/482,995, filed 10 Apr. 2017; and U.S. application Ser. No. 15/587,599, filed 5 May 2017; each of which is incorporated herein in its entirety by this reference.

3.1 System—Set of Servers

Figure 4:
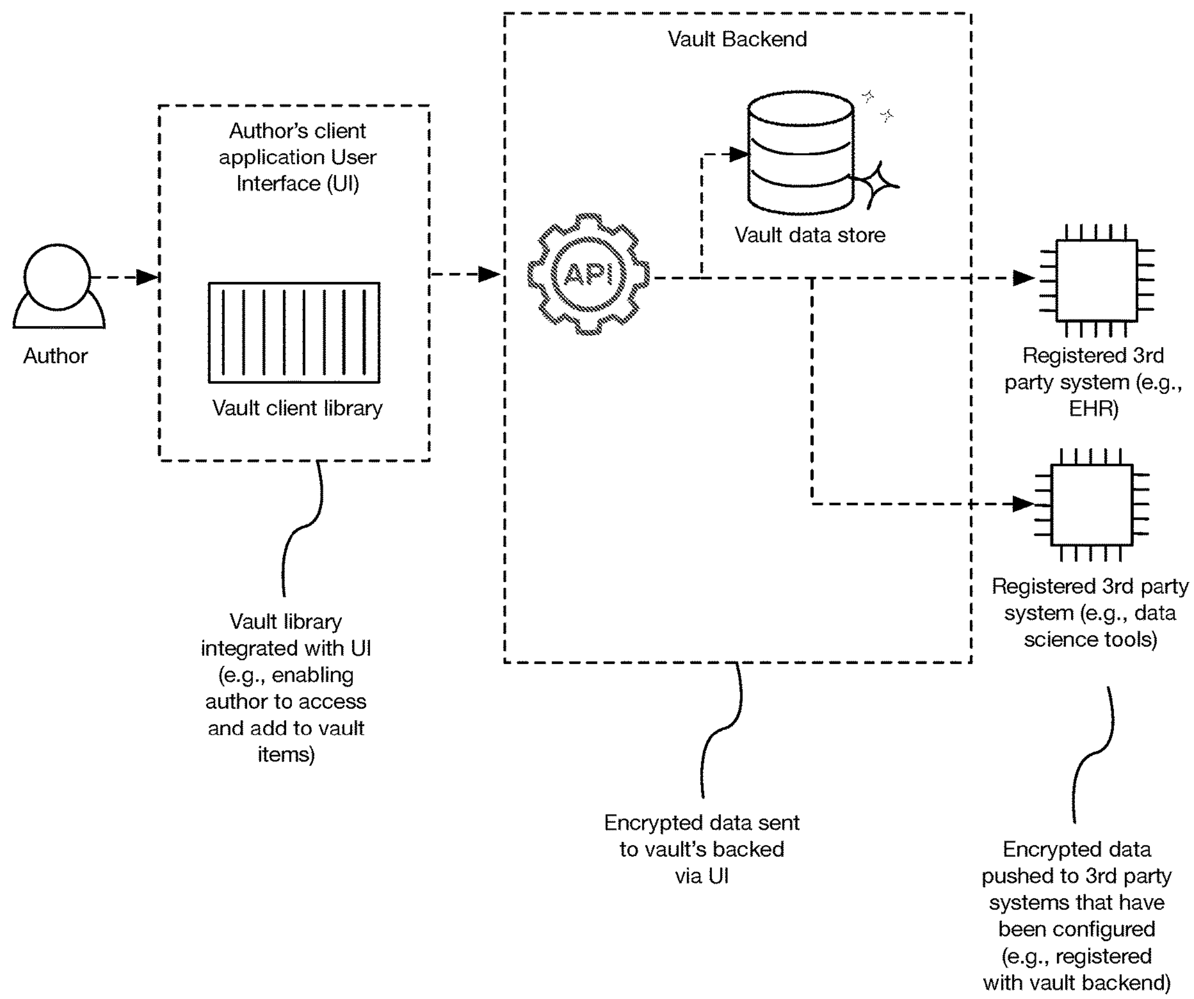
FIG. 4 depicts a variation of integration of the server with other components of the system.

The system preferably includes a set of one or more servers (e.g., first server, second server, first server and second server, etc.), which functions to store any or all of: items (e.g., encrypted items, unencrypted items, etc.), keys, keypairs (e.g., encrypted copies of users' encryption keypairs), and/or any other suitable information. At least one of the set of servers (e.g., the first server) further preferably functions to integrate with user devices and supplementary systems (e.g., as shown in FIG. 4), which can enable, for instance, the sharing of items. This server preferably includes encrypted items (e.g., as described below), but can additionally or alternatively include any other items. Any or all of the set of servers can additionally or alternatively function to store information which is unencrypted, which can function, for instance, to adhere with regulatory standards and/or other forms of compliance (e.g., to preserve copies of the data which can be reliably accessed if needed). Additionally or alternatively, the set of servers can include any other servers and/or perform any suitable functions.

The set of servers preferably include remote servers (e.g., cloud-based servers), but can additionally or alternatively include one or more local servers, any combination, and/or any other suitable servers.

The set of servers preferably includes a first server (equivalently referred to herein as the vault and/or the vault server), wherein the first server functions to receive, store, and selectively provide access to encrypted items (e.g., as described below). Additionally or alternatively, the first server can include any other items (e.g., encrypted, unencrypted, etc.).

The first server preferably includes one or more remote servers (e.g., cloud-based servers). Additionally or alternatively, the first server can include one or more local servers and/or any combination.

Any or all of the users and/or their devices are preferably registered with the first server (e.g., as described in S210), such that the users can access data from the first server (e.g., through their devices, through client applications executing on their devices, etc.). Additionally or alternatively, the system and/or method can be implemented in absence of registering users and/or their devices with the first servers, the users and/or their devices can be registered with other servers (e.g., the second server), and/or the users and/or their devices can otherwise interact with the servers. Further additionally or alternatively, 3$^{rd}$ party entities and/or systems can interact with the first server through any or all of: their own servers, their own client applications, and/or with any other components and/or tools.

The set of servers can optionally include a second server, which functions to store unencrypted versions of the data in the first server and/or any other data (e.g., encrypted data, other unencrypted data, etc.). This can in turn serve as a redundant source and/or backup of data in the first server, satisfy regulatory and/or other compliance requirements (e.g., for working with PHI, HIPAA compliance, etc.), serve as a data source which data scientists can access (e.g., on an exceptional basis only, in an extremely secure interface, in extremely limited numbers, etc.) to acquire data for training and/or retraining any or all of the models and/or algorithms used in a program and/or platform (e.g., digital health platform), and/or can perform any other functions. In some variations, such as those involving health data (e.g., PHI), the second server can function to enable compliance with any number of regulations (e.g., Health Insurance Portability and Accountability Act [HIPAA] compliance, existing regulations, custom regulations, etc.) for health information (e.g., individually identifiable health information). In specific examples, for instance, for regulatory reasons involving PHI, the data cannot only be in encrypted form with the risk of losing access to it (e.g., through lost keys).

The second server is preferably associated with no services (e.g., production services and/or other services in which individuals and/or entities can access the second server) and/or minimal services, thereby minimizing the occurrence of attacks (e.g., by hackers) to the data with within the second server. In preferred variations, for instance, only necessary data processing tasks are permitted to run in the second server. In specific examples, these tasks are for the purpose of data anonymization and de-identification, thereby creating processed data which can be stored in a server (e.g., third server) and/or database accessible by data scientists (e.g., for model development, training, etc.). Additionally or alternatively, the second server can be otherwise configured.

Figure 10:
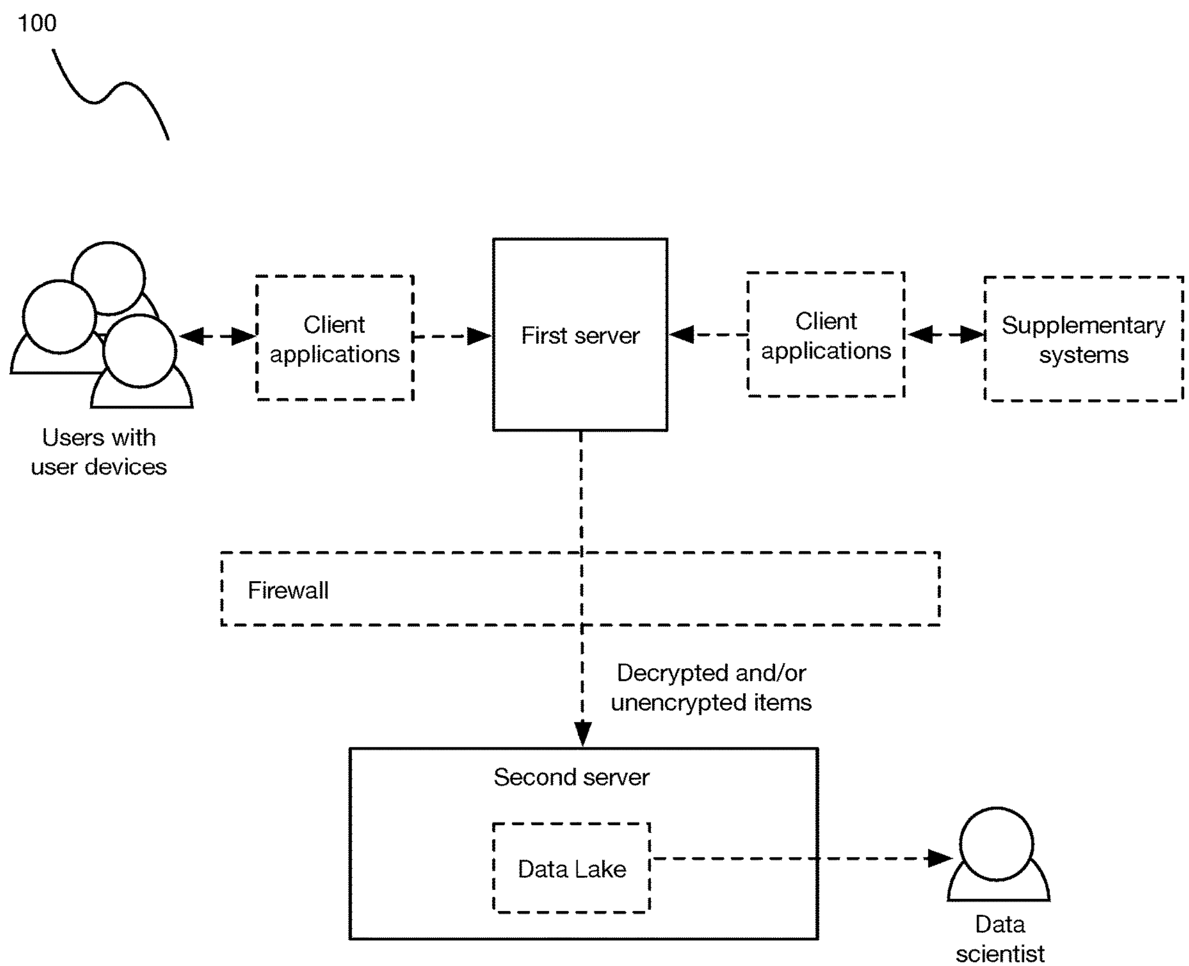
FIG. 10 depicts a schematic variation of the transmission of data from a first server to a second server.

In preferred variations (e.g., as shown in FIG. 10), for instance, the second server includes a copy of each of the items in the first server, wherein the copies of the items in the second server are decrypted (e.g., relative to the first server) and/or able to be decrypted. The data in the second server can optionally be encrypted and/or re-encrypted (e.g., with a different encryption process relative to the first server, with a uniform and/or unified encryption process, without keys distributed among users, etc.). Additionally or alternatively, the second server can include modified data relative to the first server (e.g., with identifying information removed, with metadata removed, etc.), a subset of data relative to the first server (e.g., only data with PHI, only data with PII, only data with PHI and/or PII, only data with personally identifiable information, only data with sensitive information, etc.), additional data relative to the first server, unencrypted data (e.g., wherein data is copied over to the second server prior to encryption at the first server), and/or any other data.

Figure 11:
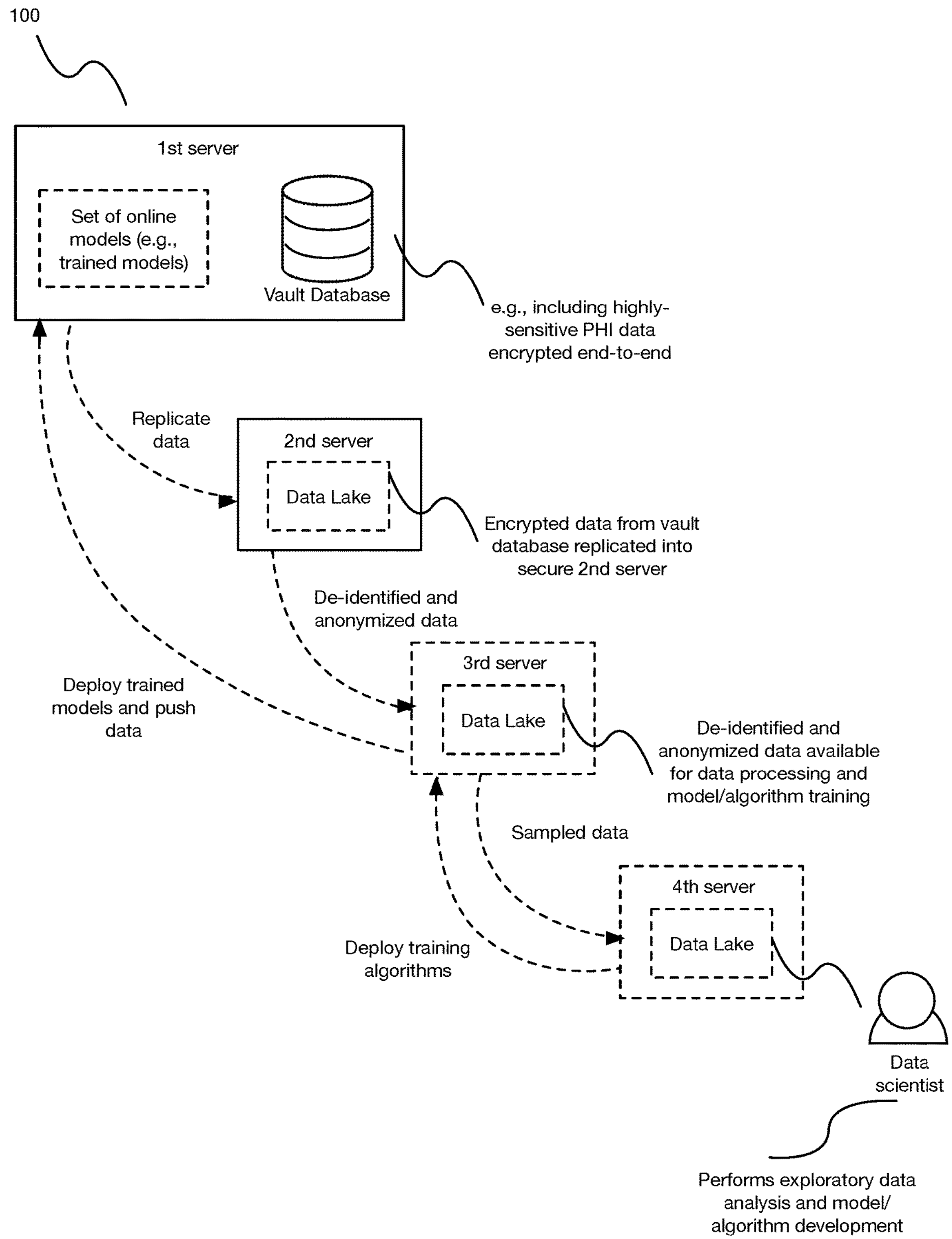
FIG. 11 depicts a schematic variation of data in a set of multiple servers.

Additionally or alternatively, the system 100 can include any number of servers or databases stemming from the second server, which can individually and/or collectively function to alter the data in the second server for any or all of: security reasons, efficiency reasons, and/or any other purposes. In some variations (e.g., as shown in FIG. 11), for instance, data from the second server is processed (e.g., de-identified, anonymized, etc.) and stored in other servers and/or databases, such that data scientists (e.g., of the platform and/or program) can use the processed data for any or all of: data processing, algorithm and/or model development, algorithm and/or model training (e.g., training, retraining, updating, testing, validating, etc.), exploratory data analysis, and/or any other processes. In specific examples, for instance, data scientists may access the second server on an exceptional basis only and instead can more readily access data which has been processed from the second server. As such, algorithms and models are preferably never trained using data with Personally Identifiable Information (PII) and/or Protected Health Information (PHI), thereby preventing PII and PHI from ever being leaked out or accessed by attackers.

In a first variation, the system 100 includes a first server which stores a set of encrypted items generated based on data created by users (e.g., in a program and/or platform), along with a subset of a set of keys used during users' interactions with the encrypted items. The subset of keys stored at the first server preferably includes a set of user keys (e.g., an encrypted user encryption keypair for each user, a plaintext user encryption public key for each user, a plaintext user signing public key for each user, etc.), a set of device keys (e.g., a plaintext device signing public key for each device registered with the first server), a set of system keys (e.g., a plaintext system encryption public key for each system registered with the first server), a set of vault item keys (e.g., an encrypted vault item encryption key for each item in the first server), and/or any other keys. In specific examples (e.g., as shown in FIG. 3E), for instance, the first server includes: an encrypted user encryption keypair for each user registered with the first server, a plaintext user encryption public key for each user registered with the first server, a plaintext user signing public key for each user registered with the first server, a plaintext device signing public key for each device registered with the first server, a plaintext system encryption public key for each system registered with the first server, and a set of vault item keys (e.g., an encrypted vault item encryption key for each item in the first server. Additionally or alternatively, the first server can store additional keys, a subset of these keys, unencrypted versions of any or all of these keys, encrypted versions of any or all of these keys, and/or any other keys.

In a second variation, the system 100 includes a second server in addition to the first server, wherein the second server includes decrypted copies of the items in the first server. The second server is preferably in 1-way communication with the first server, wherein information can be sent from the first server to the second server (e.g., through a firewall), but not from the second server to the first server. Alternatively, the first and second servers can be absent of communication, in 2-way communication, and/or otherwise configured.

In a third variation, the system 100 includes additional servers and/or databases stemming off from the second server, which include processed data (e.g., removing sensitive information, removing PHI, removing PII, etc.) relative to the second server, and function to secure provide information to data scientists (e.g., for model development and/or training).

Additionally or alternatively, the system can include only the first server, only the second server, other servers, and/or any combination of servers.

3.2 System—Set of Items

The system 100 preferably includes and/or interfaces with a set of items, wherein the set of items includes information created by users and/or systems. Additionally or alternatively, the set of items can include information created automatically (e.g., with a set of models and/or algorithms), data retrieved from other databases (e.g., from medical record databases such as EMR and/or EHR and/or PACS databases, from the internet, from social networking sites, etc.), and/or any other data used in the implementation of a program and/or platform (e.g., digital health platform, remote therapy platform, etc.).

An item refers to data, wherein the data preferably include information which can be represented in JSON and/or binary (e.g., for large objects like video) formats, but can additionally or alternatively include any other suitable data types. Examples of data include, but are not limited to, any or all of: medical records, sensor data, large files (e.g., video, recorded appointments such as recorded telehealth appointments, etc.), audio data, video data, social media data, messages (e.g., at a coaching platform, text messages, written letters, etc.), and/or any other suitable data.

Any or all of the data can include sensitive information, such as, but not limited to, any or all of: health and/or medical information (e.g., Protected Health Information [PHI], Personally Identifiable Information [PII], medical records, clinical records, notes from a therapist or other clinician, notes from a coach related to a mental health of a user, notes from a coach related to a physical health of a user, information provided by a user in digital health platform, messages exchanged between a member and a coach in a digital health platform, messages exchanged between users in a digital health platform, etc.), other personal information associated with users (e.g., financial information, home address and/or other locations, demographic information, etc.), proprietary information associated with a platform and/or program (e.g., course material of a digital health program, algorithms and/or models, protocols, coaching resources, etc.), and/or any other sensitive information.

Additionally or alternatively, any or all of the data can include non-sensitive information (e.g., publicly available information, information which is not individually identifiable, etc.) and/or any other information.

Each data piece can optionally be decomposed into 1 or more items, wherein each item represents a portion of this larger data piece. These portions, for instance, can include any or all of: fields (e.g., fields of a medical report), sections (e.g., sections of a clinical note), segments (e.g., video segment of a video clip), and/or other subsets of a larger data structure. The division of data into multiple smaller items preferably functions to: enable storage of unconventional (e.g., non-password, non-chat, etc.) data; enable the sharing of only parts of a data piece (e.g., particular sections of a medical report, particular sections of notes recorded by a coach and/or clinician in the digital health platform, etc.); and/or can perform any other suitable functions. Additionally or alternatively, any or all of the set of items can include the entire data piece (e.g., entire report, entire notes from a session, etc.), multiple data pieces, and/or any other data.

Decomposing data into items can be performed with and/or based on any or all of: a set of rules, algorithms, models (e.g., trained machine learning models, deep learning models, etc.), decision trees, user preferences and/or designations, and/or any other tools. In some variations, for instance, each type of data is prescribed a rule for which sections and/or portions become items. In additional or alternative variations, the division of data into items is performed with a set of trained models.

In some examples, for some data types, the division into items can be predetermined. In specific examples, for instance, a data type such as a medical report can be divided into items based on the predetermined different sections of the report, wherein the information in each section becomes a single item.

The set of items can additionally or alternatively be determined based on any grammatical, syntax, and/or language features, such as, for instance, any or all of: periods (e.g., to separate sentences into different items), indentations (e.g., to separate paragraphs into different items), and/or any other suitable features.

The division of data into items preferably functions to enable portions of a large record to be encrypted and shared individually and/or separately (e.g., without having to share the whole large record). Additionally or alternatively, the division of data into items can function to minimize the upkeep and processing required to frequently update large amounts of data. If users are making frequent changes to a large document or other type of data, it can be wasteful and intensive from a processing perspective (e.g., encryption, decryption, generation of new keys, etc.). Additionally or alternatively, the division into data types can be otherwise performed and/or confer any other benefits.

At least a subset of the set of items (e.g., encrypted items) is preferably stored at the first server and optionally at any other servers (e.g., decrypted versions stored at a second server, unencrypted versions stored at a second server, processed versions stored at additional servers and/or databases, etc.). Additionally or alternatively, any or all of the items can be stored at a user device, at a supplementary system, and/or at any suitable location or combination of locations. In preferred variations, an encrypted version of every item is stored at the first server.

An item can be created (e.g., as described below) at any or all of: a supplementary system, a user device, the server, another component, and/or any combination of component. Each item is preferably associated with an identifier (ID) (e.g., tag, serial number, etc.), which functions to enable items to be easily retrieved (e.g., to be shared with other users, to be read, etc.), but can additionally or alternatively be otherwise identified.

In a first set of variations, each of the set of items includes at least a portion of at least a larger data piece produced by a user and/or otherwise generated as part of a program and/or platform. In specific examples, encrypted versions of these items are stored at the first server, and decrypted versions are stored at a second server.

Additionally or alternatively, items can be otherwise stored and/or formed.

3.3 System—Set of Keys

The system 100 includes a set of keys, which function to enable any or all of: encryption of items and/or keys; decryption of items and/or keys; signing of items and/or keys; the creation and/or maintenance of an audit log; and/or can enable any other functions.

The set of keys are preferably associated with a set of users, wherein the set of users can retain, view, share, access, distribute, and/or otherwise interact with any or all of the set of items. The set of users can include humans (equivalently referred to herein as individuals), systems, and/or any other suitable entities (e.g., robots) or combination of entities.

All users are preferably associated with (e.g., are assigned, share and receive data with, etc.) both public and private keys (e.g., as described below), wherein at least a portion of these (e.g., encrypted public-private keypair, plaintext public keys, etc.) are further preferably registered with (e.g., and stored at, and a copy stored at, etc.) the first server. At least a portion of the set of keys are further preferably not stored at the first server (or any other servers), and instead held by users. These keys preferably include the master encryption keys and master signing keys (e.g., as described below). Additionally or alternatively, the users can have any other suitable keys and/or combination of keys.

The users can be any or all of: patients; participants (equivalently referred to herein as members) in a platform/program (e.g., digital health program, mental health coaching program, physical health coaching program, etc.); coaches in a platform/program; supervisors (e.g., coach supervisors) in a platform/program; clinicians (e.g., therapists, psychiatrists, psychologists, primary care physicians, specialty physicians, surgeons, etc.); healthcare facilities and/or associated databases (e.g., Picture Archiving and Communication System [PACS]); and/or any other suitable individuals and/or entities.

In some variations, such as those involving a remote coaching platform (e.g., a digital health platform), the set of users includes any or all of: a set of members receiving care (e.g., remote coaching, remote clinical care, remote therapy, remote group therapy, conversation and community with other members, etc.) at the platform; a set of coaches interacting with the members and/or other coaches and/or clinicians and/or supervisors (e.g., sending and receiving messages with the members, providing materials to the members, having calls with the members, tracking the member's progress and/or setting or revising goals of the members; etc.); a set of clinicians (e.g., doctors, therapists, coaches with clinical training, etc.) interacting with the members and/or coaches and/or supervisors and/or other clinicians (e.g., sending and receiving messages with the members, sending and receiving members with the coaches, providing materials to the members, having calls with the members, providing therapy to the members, prescribing medication to the members; providing referrals to the members; tracking the member's progress and/or setting or revising goals of the members); a set of supervisors who monitor and/or guide the coaches and/or clinicians (e.g., by reviewing messages sent by coaches and/or clinicians, by reviewing members' progress in reaching their goals, etc.); and/or any other users.

In specific examples, each member is assigned one or more coaches who provide coaching to help the member achieve a set of goals (e.g., mental health goals, physical health goals, career goals, etc.). Additionally, the member can optionally be assigned one or more clinicians who can provide therapy or other forms of clinical care to the members. A set of supervisors can optionally be associated with any or all of the clinicians and/or coaches to monitor their performance in helping the member achieve his or her goals. Additionally or alternatively, the users can include and/or interface with any individuals.

Additionally or alternatively, the set of users can include and/or interface with any or all of those described in any or all of: U.S. application Ser. No. 13/969,349, filed 16 Aug. 2013; U.S. application Ser. No. 14/839,232, filed 28 Aug. 2015; U.S. application Ser. No. 15/005,923, filed 25 Jan. 2016; U.S. application Ser. No. 15/069,163, filed 14 Mar. 2016; U.S. application Ser. No. 15/265,454, filed 14 Sep. 2016; U.S. application Ser. No. 15/482,995, filed 10 Apr. 2017; and U.S. application Ser. No. 15/587,599, filed 5 May 2017; each of which is incorporated herein in its entirety by this reference.

Any or all of the users can serve as authors, where authors refer to users who create data, such as any or all of: clinicians (e.g., who write clinical notes, who write messages to members and/or coaches, who have video conferences with members, etc.), coaches (e.g., who write messages to participants, who take notes of participant progress, who administer surveys to members, who write message to supervisors and/or other coaches and/or clinicians, who have video conferences with members, who provide content to members, etc.), participants in a coaching platform (e.g., who write messages to coaches, who input data into a dashboard, who write in a journal such as an electronic journal, etc.), and/or any other suitable users who create data.

In some variations, the set of users includes a set of supervisors, wherein supervisors refer to users who have a relatively large amount of data, such as read-only data, shared with them. The supervisors are preferably able to do everything that an author can do. Additionally or alternatively, the supervisors can be part of the author group, the set of users can be absent of a set of supervisors, the supervisors can be able to perform a subset of actions as the authors, and/or the supervisors can be otherwise characterized. In a set of variations, the set of supervisors includes, for instance, but is not limited to, any or all of: heads of clinical operations (e.g., who can view all clinical notes across the organization); coach supervisors (e.g., who can view messages and other information sent by the coaches they supervise); and/or any other suitable users.

The users can preferably participate in and/or perform any or all of: creating data (e.g., as described above); encrypting data at one or more devices; sharing data they create with other users and/or systems; and reading data they created and/or has been shared with them (e.g., as described below). Additionally or alternatively, the authors can engage in any other suitable tasks.

The set of users can optionally additionally or alternatively include a set of supplementary systems (e.g., 3$^{rd}$ party systems), wherein the supplementary systems preferably include 3$^{rd}$ party applications (e.g., client applications) and/or data storage that the system 100 securely pushes data to and/or otherwise interacts with (e.g., receives items from). The supplementary systems can include, for instance, but are not limited to, any or all of: a data lake where anonymized datasets are collected for data science purposes (e.g., to be processed and monitored to improve the method 200); 3rd party application programming interfaces (APIs) (e.g., to push medical billing information into); other servers and/or data storage sites (e.g., PACS); and/or any other suitable locations.

Any or all of the users and/or supplementary systems can be assigned to one or more groups, wherein the groups function to enable easy sharing of items that are most relevant to each user (e.g., wherein users can only access items created by users in these groups, wherein users can most easily access items created by users in these groups, etc.). Additionally or alternatively, the groups can function to organize items (e.g., in the first server) and/or perform with any other functions. Further additionally or alternatively, the system and/or method can be implemented in absence of groups.

In variations involving groups, each group is preferably associated with a set of keys, further preferably a group public-private keypair, wherein items and/or copies of items at the first server can be encrypted with any or all of the group's keys, thereby enabling these items to be easily shared with and/or accessed by other users of the groups. In specific examples, for instance, an encrypted version of the group's public-private keypair is registered with and optionally stored at the first server.

In a preferred set of variations, each coach is assigned to a set of groups, wherein the set of groups preferably includes a first group including a set of coaches that the coach interacts with (e.g., coaching the same member) and a second group including a set of clinicians that the coach interacts with (e.g., clinicians assigned to the same member(s) as the coach). Additionally or alternatively, clinicians can be assigned groups (e.g., a first group including coaches he or she interacts with, a second group including other clinicians he or she interacts with, both, etc.). Further additionally or alternatively, supervisors can be assigned groups (e.g., a first group including coaches that the supervisor supervises, a second group including clinicians that the supervisor supervises, both, etc.). Further additionally or alternatively, members can be assigned groups (e.g., a first group including coaches that the member is coached by, a second group including clinicians that member interacts with, both, etc.). Further additionally or alternatively, users can be otherwise assigned to groups and/or groups can otherwise be assigned to any or all of the users. In some variations, for instance, a group can be created for each member of the digital health program, wherein each coach and/or clinician and/or other user can only view data associated with particular members that he or she is interacting with.

The set of keys can optionally additionally or alternatively include a set of master keys associated with each user and/or each supplementary system, wherein the master key functions to encrypt and/or decrypt the user's and/or supplementary system's encryption keypair. An encrypted copy of the encryption keypair is preferably uploaded to the first server, which functions to enable rotation of the user's encryption keypair (e.g., in a routine fashion for security purposes, in an event that the user loses access to his master keys, in an event that the user's master key gets out, etc.) without forcing the user to keep copies of all of their previous keys in order to decrypt historical data, as older versions of the encrypted copy of the encryption keypair will be kept in the server. This further preferably functions to make it easy to distribute the encrypted copy of the encryption keypair among various devices associated with the user (e.g., laptop, mobile phone, desktop, tablet, clinician workstation, etc.).

Figure 3A:
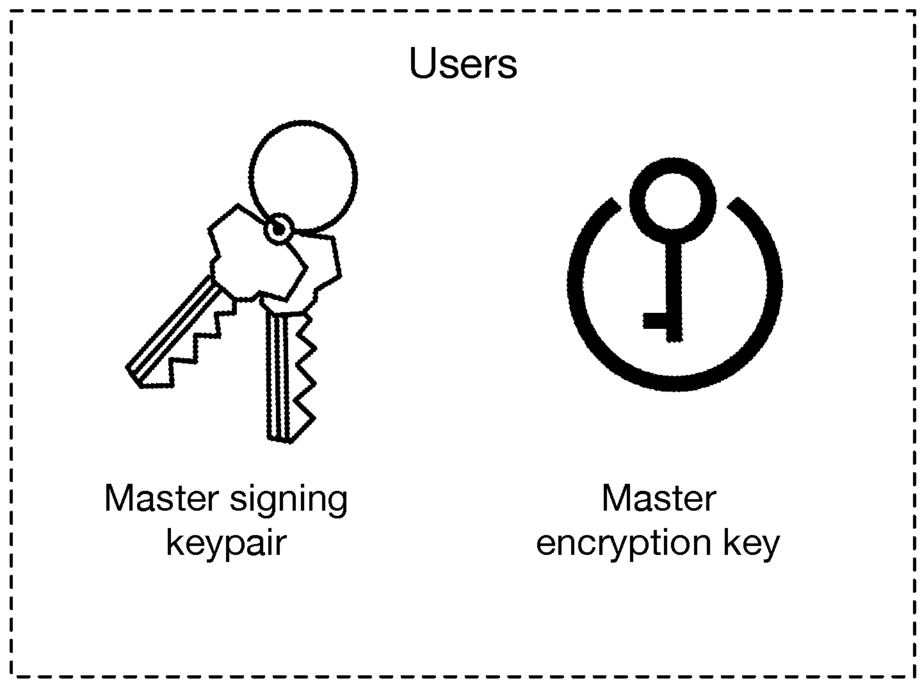
FIGS. 3A-3E depict a variation of the system and associated keys and keypairs.

In preferred variations (e.g., as shown in FIG. 3A), each user has a set of master keys and/or keypairs, which function to enable users to ultimately access items from the first server. Additionally or alternatively, the set of master keys and/or keypairs can function to enable the user to sign encrypted items (e.g., for verification purposes). The set of master keys and/or keypairs preferably includes a master signing public-private keypair (equivalently referred to herein as a master signing keypair), which is used to authenticate items and/or authenticate, register, and revoke user's devices; and a master encryption key, which encrypts the user's encryption keypair such that the encrypted version of the encryption keypair can be stored at the first server. The master encryption key and the master signing keypair are preferably held by the user and not sent to the server. This configuration of keys and whether or not each is sent to the server or held by the user can confer a number of benefits in different types of potential data breaches by an attacker. In a first scenario, for instance, in which a master signing key was leaked, an attacker could theoretically authenticate with the server and download encrypted items. Without having possession of the master encryption key or the user's private key, however, the attacker could not decrypt any of the items. In a second scenario in which a master encryption key is leaked and/or the user's private encryption key is leaked, an attacker could theoretically decrypt the user's encryption keypair and thus all items shared and/or created by that user. The attacker would first, however, need to obtain a copy of the encrypted data by either breaking into the server or obtaining the user's master signing key so they could login to the server.

Additionally or alternatively, the system can include other master keys and/or master keypairs, the master keys can perform any other suitable functions, the keys can be absent of master keys, and/or the keys can be otherwise configured.

Figure 3B:
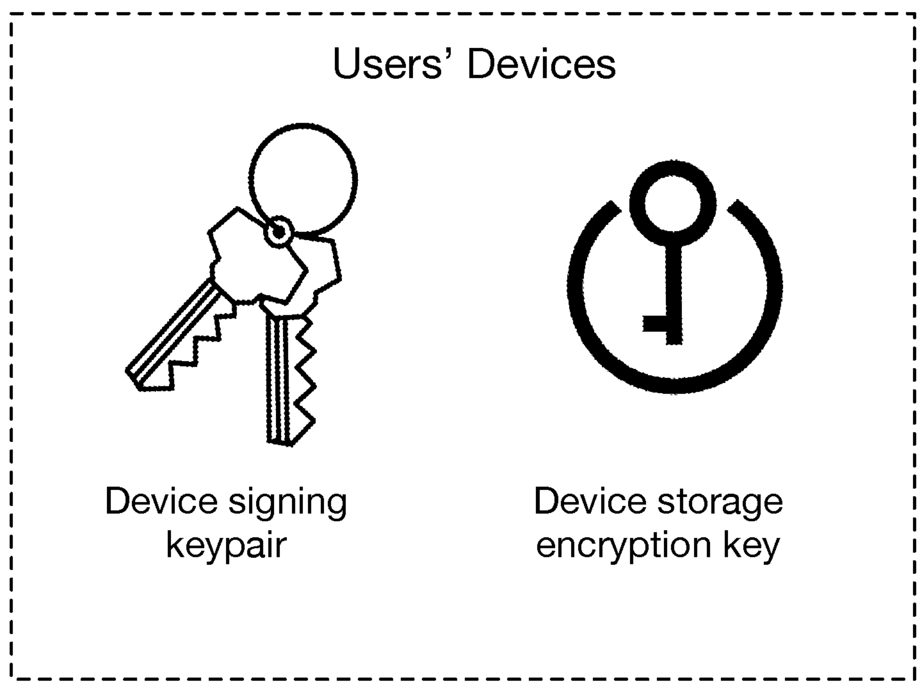

The set of keys further preferably includes a set of device keys (e.g., as shown in FIG. 3B) associated with each of the user devices, wherein the device keys further preferably include a device signing keypair to authenticate the device with the server and a device storage encryption key, which encrypts any vault-server-related keys on the device (e.g., only for non-browser environments, in any environments, etc.). Additionally or alternatively, devices can be associated with any other suitable keys, keypairs, and/or combination of keys and keypairs.

Figure 3C:
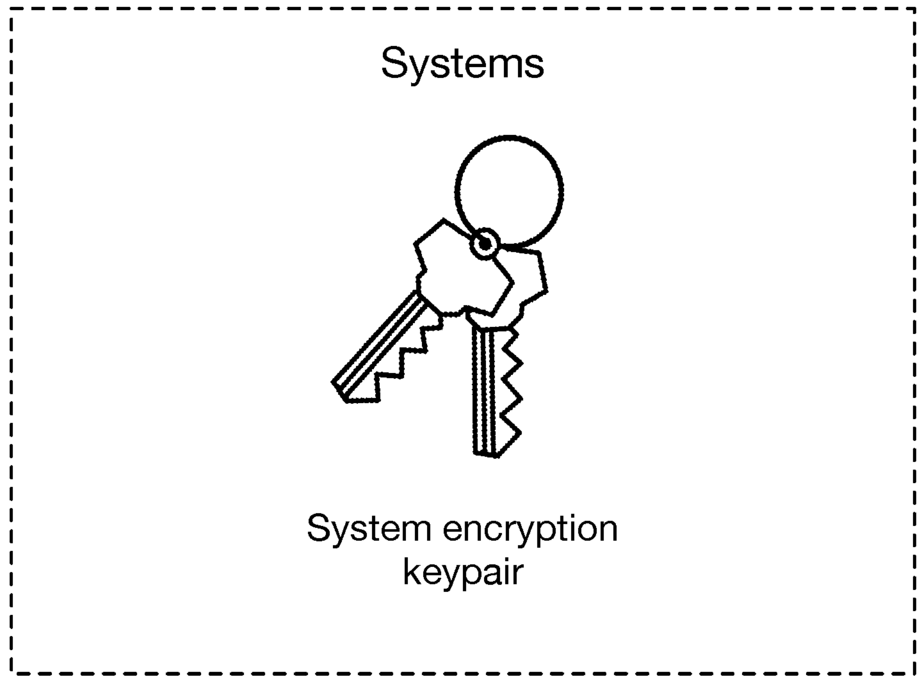

The set of keys further preferably includes a set of system keys (e.g., as shown in FIG. 3C) associated with each of the supplementary systems, further preferably a system encryption keypair for each supplementary system which is used to share server items with the supplementary system. Additionally or alternatively, systems can be associated with any other suitable keys, keypairs, and/or combination of keys and keypairs.

Figure 3D:
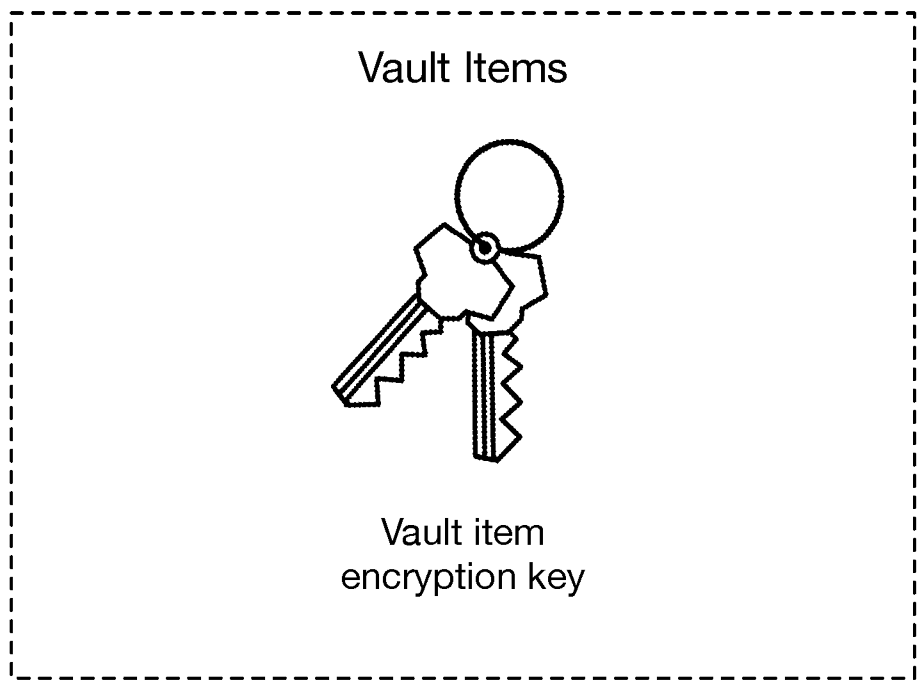
Figure 3E:
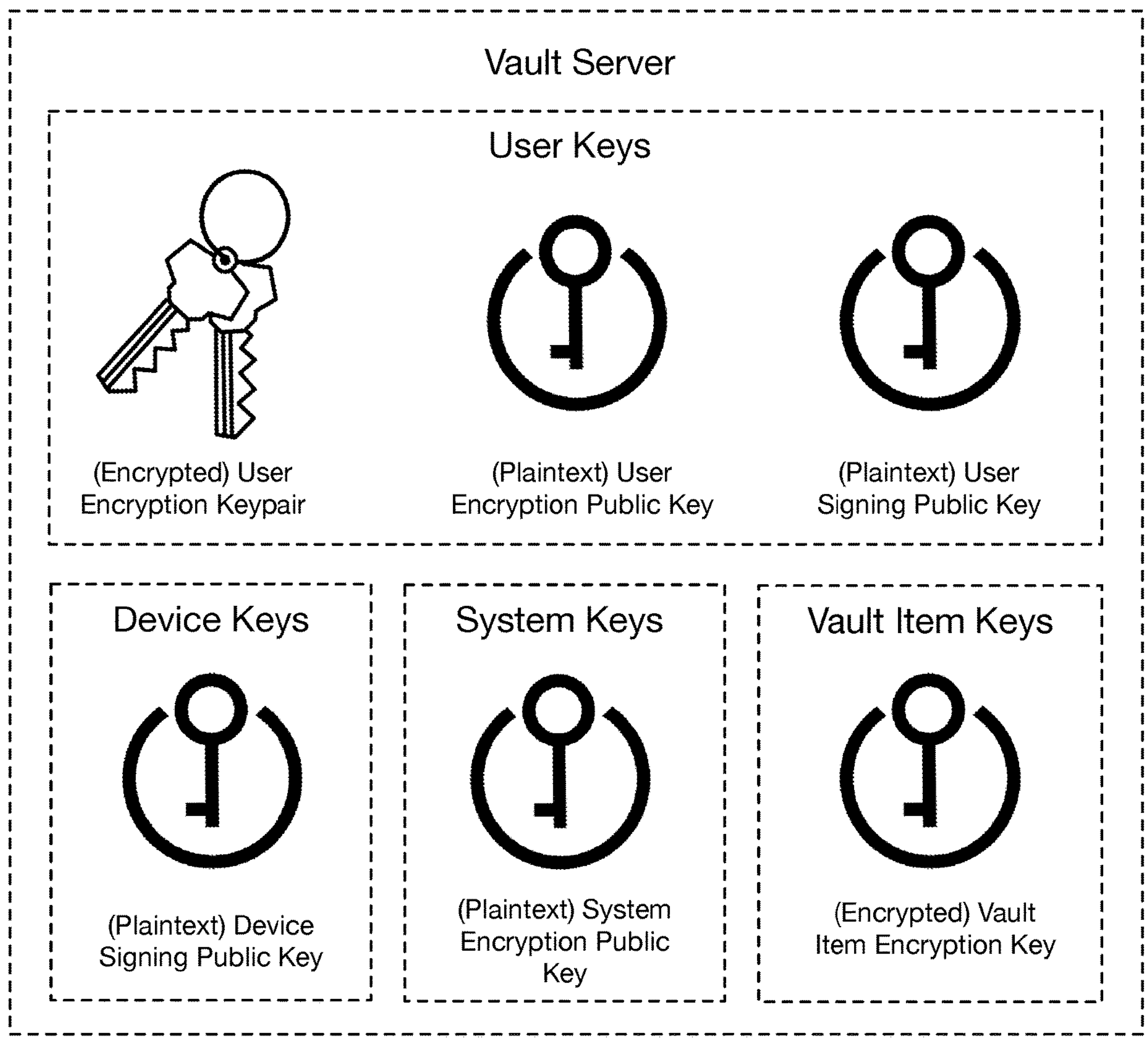

The set of keys further preferably includes a set of item keys (e.g., as shown in FIG. 3D) associated with each item, further preferably a set of server item encryption keys (equivalently referred to herein as vault item encryption keys), which are used to encrypt that particular item's data at the first server (e.g., as described below). Additionally or alternatively, items can be associated with any other suitable keys, keypairs, and/or combination of keys and keypairs.

The encryption of items with item keys functions to facilitate data sharing. An item can be shared, for instance, by securely sharing its item key. This can further function to require only keeping one copy of an item's data (e.g., at a server, at cloud storage, in a local server, etc.), rather than multiple copies (e.g., a copy for every person with access).

When the data of an item are updated and/or altered, the new data only has to be written once, rather than multiple times (e.g., for multiple copies of an item, for the number of individuals with access to the item, etc.). This further functions to enable an item key to be easily rotated, as a new key can be generated, the item data can be encrypted again under the new key, and the new key can be re-shared.

The encryption of items with item keys further functions to mitigate risks related to key deterioration. In some use cases, for instance, encryption keys can only encrypt so much data before they risk leaking sensitive information. Having a unique encryption key per item makes this risk easy to manage as compared with encrypting multiple items' worth of data with the same item key.

Additionally or alternatively, the set of keys further preferably includes a set of keys (e.g., as described above, additional to those described above, alternative to those described above, etc.) stored at the server. In preferred variations (e.g., as shown in FIG. 3E), the keys stored at the server include: a set of user keys, the set of user keys including an encrypted user encryption keypair (e.g., encrypted with the user's master encryption key), a plaintext user encryption public key used to share items with this user, and a plaintext user signing public key used to verify requests to add/evoke a user's device; a set of device keys, wherein the set of device keys includes plaintext device signing public keys used to authenticate the devices with the server; a set of system keys including plaintext system encryption public keys used to share server items with the supplementary systems; and a set of vault item keys including a set of encrypted vault item encryption keys, which are encrypted with the recipient's (e.g., user, author, supervisor, supplementary system, etc.) public key. Additionally or alternatively, any or all of these keys can be stored elsewhere, the server can store other keys, and/or any other suitable configuration and/or arrangement of keys can be implemented.

Additionally or alternatively, the set of keys includes any other suitable keys, keypairs, and/or combination of keys and keypairs.

3.4 System—User Devices

The system preferably interfaces with a set of user devices, each user device associated with one or more users, wherein the set of user devices can be registered with the first server (and/or any other services) and be used in any or all of: the creation of items, the sharing of items, the receipt of items, the reading of items, and/or any other suitable uses.

The user devices can execute any number of client applications of the supplementary systems, client applications independent of the supplementary systems, and/or can implement and/or include any other suitable software. As such, the system 100 can further include any number of Application Programming Interface (API) layers in communication with the client application(s). An API layer can function, for instance, to retrieve keys, decrypt keys, encrypt keys and/or items, and/or otherwise enable the client application to interact with the first server.

The set of user devices can include, but is not limited to, any or all of: mobile devices (e.g., mobile phones, tablets, laptops, smart watches, etc.), desktop devices (e.g., desktop computer), workstations (e.g., clinical workstations), and/or any other suitable devices.

Examples of the user device include, for instance, any or all of: a tablet, smartphone, mobile phone, laptop, watch, wearable device (e.g., glasses), or any other suitable user device. The user device can include power storage (e.g., a battery), processing systems (e.g., CPU, GPU, memory, etc.), user outputs (e.g., display, speaker, vibration mechanism, etc.), user inputs (e.g., a keyboard, touchscreen, microphone, etc.), a location system (e.g., a GPS system), sensors (e.g., optical sensors, such as light sensors and cameras, orientation sensors, such as accelerometers, gyroscopes, and altimeters, audio sensors, such as microphones, etc.), data communication system (e.g., a WiFi module, BLE, cellular module, etc.), or any other suitable components.

3.5 System—Key management System

The system can optionally include and/or interface with an end user key management system, which functions to make it easier for users to interact with the system and not be at risk of losing keys. The end user key management can include any or all of: a password management system (e.g., integrating with an existing $3^{rd}$ party password management system, enterprise password manager, etc.), a secure password generation system, a QR code which the user can present as any or all of his or her master keys, and/or any other suitable system.

In a first variation of the system 100, the system includes: a set of items, each of the set of items representing a portion of a larger data structure; a set of keys and keypairs associated with the set of items, a set of users and/or user devices, and a set of supplementary systems; a server (e.g., remote server) which stores a set of items and encrypted copies of a subset of the set of keys and keypairs; wherein the system interfaces with the set of user devices, the set of supplementary systems, and optionally includes and/or interfaces with an audit log.

Figure 9:
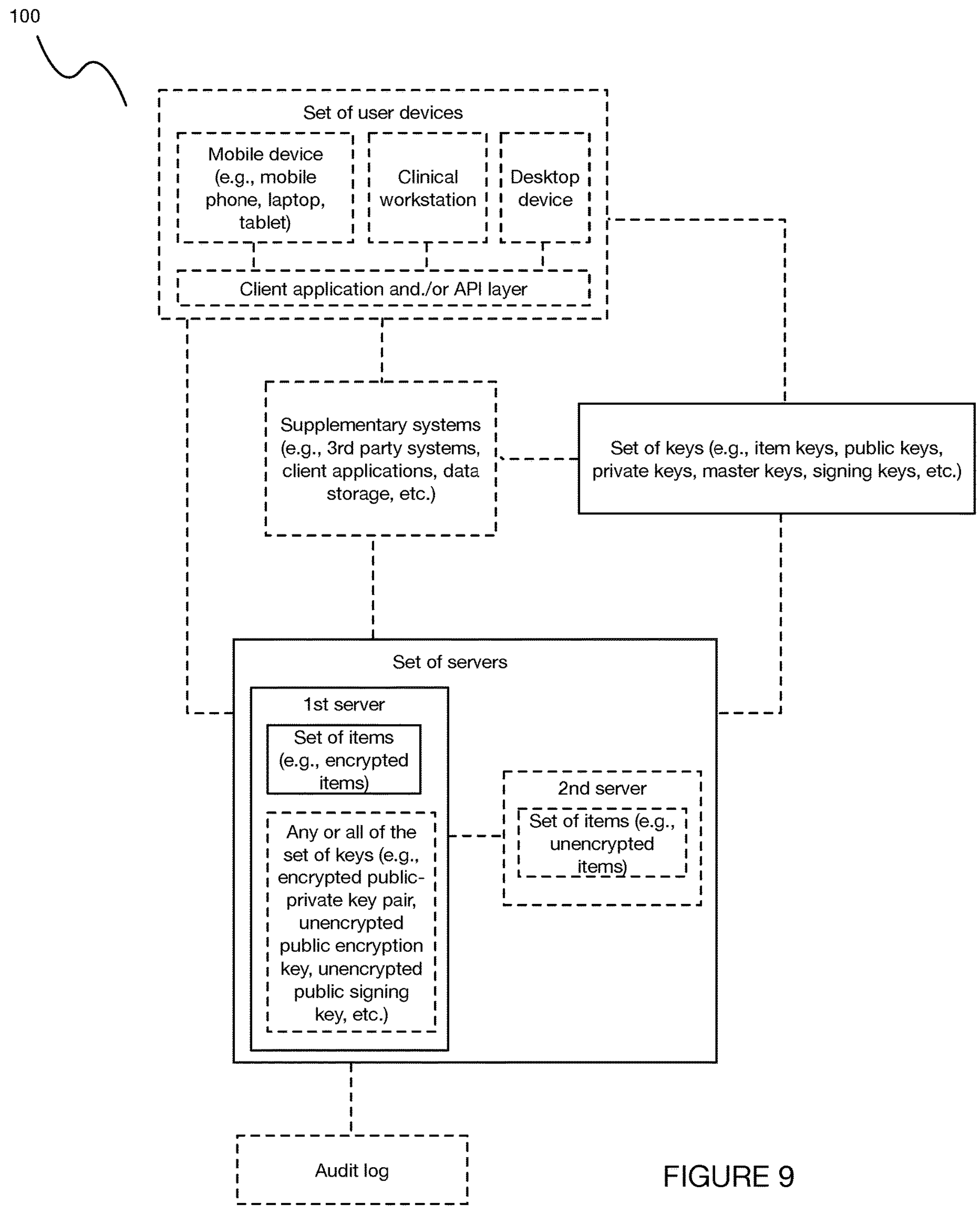
FIG. 9 depicts a schematic variation of a system for digital health data encryption.

In a specific example of the system (e.g., as shown in FIG. 9), the system 100 includes a set of keys; a set of servers including at least a first server, wherein the first server stores an encrypted set of items, and optionally a second server, wherein the second server includes decrypted versions of the set of items. Additionally the system can include and/or interface with any or all of: an audit log to record actions associated with the $1^{st}$ server and optionally any or all of the other servers; a set of user devices; client applications and/or associated API layers (e.g., executing on the user devices); supplementary systems, and/or any other components.

In an additional specific example, the second server can pass processed versions of the set of decrypted items to an additional set of servers and/or databases.

In an alternative specific example, the set of servers can include only the first server.

Additionally or alternatively, the system 100 can include any other suitable components and/or combination of components.

4. Method 200

As shown in FIG. 2, a method 200 for data encryption and/or sharing includes any or all of: encrypting items S230, sharing items S240, and reading items S250. The method 200 can optionally additionally or alternatively include any or all of: performing a registration process S210, creating items S220, restricting access of users and/or supplementary systems to items, and/or any other suitable processes. Any or all of these processes can be individually performed, performed together (e.g., creating items can include encrypting items), or performed in any suitable combination. The method 200 is preferably performed with a system 100 as described above, but can additionally or alternatively be performed with any other suitable system(s).

The method 200 can additionally or alternatively include and/or interface with any or all of the methods, processes, embodiments, and/or examples as described in any or all of: U.S. application Ser. No. 13/969,349, filed 16 Aug. 2013;

U.S. application Ser. No. 14/839,232, filed 28 Aug. 2015; U.S. application Ser. No. 15/005,923, filed 25 Jan. 2016; U.S. application Ser. No. 15/069,163, filed 14 Mar. 2016; U.S. application Ser. No. 15/265,454, filed 14 Sep. 2016; U.S. application Ser. No. 15/482,995, filed 10 Apr. 2017; and U.S. application Ser. No. 15/587,599, filed 5 May 2017; each of which is incorporated herein in its entirety by this reference.

The method 200 is preferably performed with a system 100 as described above, but can additionally or alternatively be performed with any other suitable system(s). The method 200 is further preferably performed in accordance with facilitating the storage and sharing of sensitive information, further preferably health information (e.g., mental health information, physical health information, etc.), associated with members of a digital health platform. In specific examples, for instance, the information is collected from any or all of: coaches (e.g., clinical coaches, non-clinical coaches, etc.), supervisors (e.g., who supervise coaches), members, and/or any other individuals participating in a digital health program which aims to provide remote care (e.g., coaching, therapy, conversation, etc.) to the members. Additionally or alternatively, the information can be collected from within a healthcare system (e.g., from a database of medical records, from an Electronic Medical Record [EMR] database, from a Picture Archiving and Communication System [PACS] database, from an Electronic Health Record [EHR] database, etc.) and/or any other information, sensitive or not, can be collected and processed (e.g., shared, read, encrypted, etc.) during the method 200.

The method functions to encrypt multiple different types, sizes, and/or other attributes of data. The method further preferably functions to enable these data to be securely shared between and among various different users and supplementary systems in limited and specific ways, which in turn functions to prevent the possibility of a massive data breach through any of these points of entry. Additionally or alternatively, the method 200 can function to perform any or all of: enabling the sharing of highly granular data (e.g., specific fields, specific fields of a medical record, specific sections of a medical report, specific sections of a clinical note, specific sections of a coach assessment, etc.); maintaining (e.g., automatically maintaining) an audit log of all shared data and/or operations with strong cryptographic guarantees; and/or the method 200 can perform any other suitable functions.

4.1 Method: Performing a Registration Process S210

The method 200 can optionally include performing a registration process S210, which functions to register one or more users, devices, and/or other entities (e.g., 3$^{rd}$ party applications, 3$^{rd}$ party databases, etc.) with the system (e.g., system 100). Additionally or alternatively, S210 can function to validate one or more entities, provide encryption keys and/or the ability to create encryption keys to one or more entities, and/or can perform any other suitable functions.

S210 is preferably performed initially for each user and/or each of his or her devices (equivalently referred to herein as user devices) (e.g., mobile user devices such as smartphones, tablets, personal computing devices, laptops, etc.), but can additionally or alternatively be performed at any or all of: multiple times during the method 200, later in the method 200, in response to another process of the method 200, in parallel with another process of the method 200, upon request and/or initiation by the user, and/or at any other time(s). Further additionally or alternatively, S210 can be performed during an onboarding of a 3$^{rd}$ party entity (e.g., 3$^{rd}$ party system, application, database, etc.) and/or at any other times.

The registration process can optionally include registering a user S212 (equivalently referred to herein as creating a user), which functions to enable a user to begin accessing (e.g., reading), sharing, and/or otherwise interacting with data. In preferred variations, registering the user includes: generating a set of keys associated with the user (e.g., master keys/keypairs, signing keys/keypairs, encryption keys/keypairs, etc.); optionally prompting the user to store keys not sent to the server (e.g., master keys/keypairs) securely; creating an item out of a keypair (e.g., encryption keypair, keypair stored at the server, etc.) and using a key not stored at the server as the item's encryption key (e.g., master encryption key); and uploading public keys (e.g., public signing key, public encryption key, etc.) and the encrypted user encryption keypair item to the server. Additionally or alternatively, registering the user can include any other suitable processes.

In a set of specific examples, registering a user includes: generating a master signing keypair, master encryption key, and user encryption keypair; prompting the user to store the master keys securely; creating a server item out of the user encryption keypair and using the master encryption key as the item's encryption key; and uploading the public signing key, public encryption key, and encrypted user encryption keypair item to server.

Registering a user can optionally additionally or alternatively include registering one or more supplementary systems with the first server (e.g., a backend of the first server), which preferably includes: uploading the supplementary system's public key and choosing how the supplementary system will receive data; pushing encrypted items and encrypted item keys from the server to the supplementary system via the chosen mechanism; at the supplementary system, decrypting the item key with its private encryption key; at the supplementary system, decrypting the item with its item key; and at the supplementary system, processing the item. Additionally or alternatively, receiving items at the supplementary system can include any other suitable processes or combination of processes involving any suitable keys.

The method 200 can optionally include registering a device S214, which functions to enable that device and/or a client application executing on the device to share, receive, create, and/or otherwise interact with data. In preferred variations, registering the device includes: generating a set of device keys/keypairs (e.g., device signing keypair, device storage encryption key, etc.); encrypting a device keypair (e.g., device signing keypair) with a device key (e.g., device storage encryption key); optionally placing the device key in storage (e.g., placing the device storage encryption key in device storage); optionally having a user associated with the user device sign a request to trust this device using a keypair of the user (e.g., using their master signing keypair by scanning a QR code) and sending the request to the server; and at the server, verifying the signature using a public key of the user (e.g., the user's master signing public key). Additionally or alternatively, registering the device can include any other suitable processes.

In a set of variations, registering a new device includes: generating a device signing keypair and device storage encryption key; encrypting the device signing keypair with the device storage encryption key; placing the device storage encryption key in secure storage of the device; having the user sign a request to trust the device using the user's master signing keypair (e.g., by entering their signing keypair through scanning a QR code); sending the request to the server; and at the server, verifying the signature using the user's master signing public key.

Additionally or alternatively, any parts of the system can be registered, the method 200 can be performed in absence of any or all of S210, and/or any or all of S210 can be otherwise suitably performed.

4.2 Method: Creating Items S220

The method 200 can optionally include creating one or more items S220, which functions to create items (equivalently referred to herein as data items and/or vault items and/or server items) which ultimately enable information to be securely stored, shared, read, and/or otherwise processed by the system or interacted with by one or more users. Additionally or alternatively, S220 can perform any other suitable functions.

Any or all of the items are preferably created based on data created and/or generated by users while engaging (e.g., writing and sending messages, creating content, sending content to a member, etc.) with a platform and/or program. Additionally or alternatively, items can be created from data which is automatically generated (e.g., by a trained model), any combination, and/or any other data.

Creating items S220 can optionally include diving data into items (e.g., as described above). This is preferably performed without user input and after the user creates and/or generates the data, but can additionally or alternatively be otherwise performed.

S220 can optionally additionally or alternatively include duplicating any or all of the items. This can function to create items (e.g., unencrypted items) to be stored at a second server. Alternatively, these items for the second server can be performed in response to S230 (e.g., followed by a decryption process). Duplicating any or all of the items can additionally or alternatively function to create copies of the items which are encrypted individually for each specified and/or potential recipient of the item (e.g., for sharing items as described below). This can include, for instance, creating an item for each user in the group associated with the author. Additionally or alternatively, this can include creating an item for each recipient specifically designated by the author.

S220 can optionally additionally or alternatively include updating items (e.g., based on author edits), deleting items (e.g., only if the item is in a draft stage), and/or any other processes.

4.3 Method: Encrypting Items S230

The method 200 preferably includes encrypting items (e.g., of a user, of an author, of a supervisor, of a supplementary system, at a device, etc.), which functions to enable the items to be securely stored within the first server. Additionally or alternatively, S230 can function to enable the items to be securely shared among users, enable an item to read by the author who created the item, read by other users (e.g., other users in a set of groups associated with the author), trigger the recording of an entry associated with the item in an audit log, and/or can perform any other suitable functions.

S230 is preferably performed in response to and based on S220, but can additionally or alternatively be performed in response to another process of the method 200, multiple times during the method 200, in absence of S220, in parallel with any processes of the method 200 (e.g., S220), and/or at any other suitable times during the method 200. In preferred variations, for instance, S230 is performed after an item is created and contemporaneously with (e.g., overlapping with, partially overlapping with, immediately prior to, immediately after, etc.) the item being uploaded to the first server. Additionally or alternatively, S230 can be performed at any other time(s).

Items (and optionally keys, keypairs, and/or other encrypted components) are preferably encrypted through envelope encryption processes, but can additionally or alternatively be encrypted through any other suitable encryption processes.

Each item is preferably encrypted with a unique item key, wherein the unique item is generated at the device (e.g., at the API layer of a client application executing on the device) of the author who created the item. Additionally or alternatively, a unique item key can be generated at the first server, at another server, and/or at any other locations. The item key is preferably a symmetric key, which functions to minimize deterioration of the item key, but can additionally or alternatively include an asymmetric key and/or any other keys.

The item key is further preferably encrypted, preferably with a public encryption key. This is preferably performed at the user's device (e.g., at an API layer of a client application), but can additionally or alternatively be performed at the first server and/or at any other server(s). In preferred variations, for instance, the item key is encrypted with a public encryption key associated with the author, which can function to enable the author to read (e.g., as described below) his or her own items. Additionally or alternatively (e.g., for sharing items in S240), the item key (and/or an item key of a copy of the item) can be encrypted with another user and/or system's public encryption key, such as that of a recipient (e.g., recipient explicitly indicated by the author, potential recipient such as a user in any or all of the groups assigned to the user, etc.). Further additionally or alternatively, the item key can be otherwise encrypted and/or unencrypted, and/or S230 can be performed in absence of this sub-process.

The encrypted item and its encrypted item key are further preferably signed with a private signing key of the author, which functions to enable verification of the item at the first server. The private signing key is preferably pulled down to the device (e.g., at an API layer of the client application) using the author's master key, but can additionally or alternatively be otherwise used. Additionally or alternatively, this can function to add an entry to an audit log and/or perform any other function(s).

S230 further preferably includes uploading this information (e.g., signed encrypted item and signed encrypted item key) to the first server. At the first server, the author's public signing key is preferably used to verify the uploaded information. Additionally or alternatively, a recipient's public signing key and/or any other key(s) stored at the first server can be used in this verification process.

Figure 5:
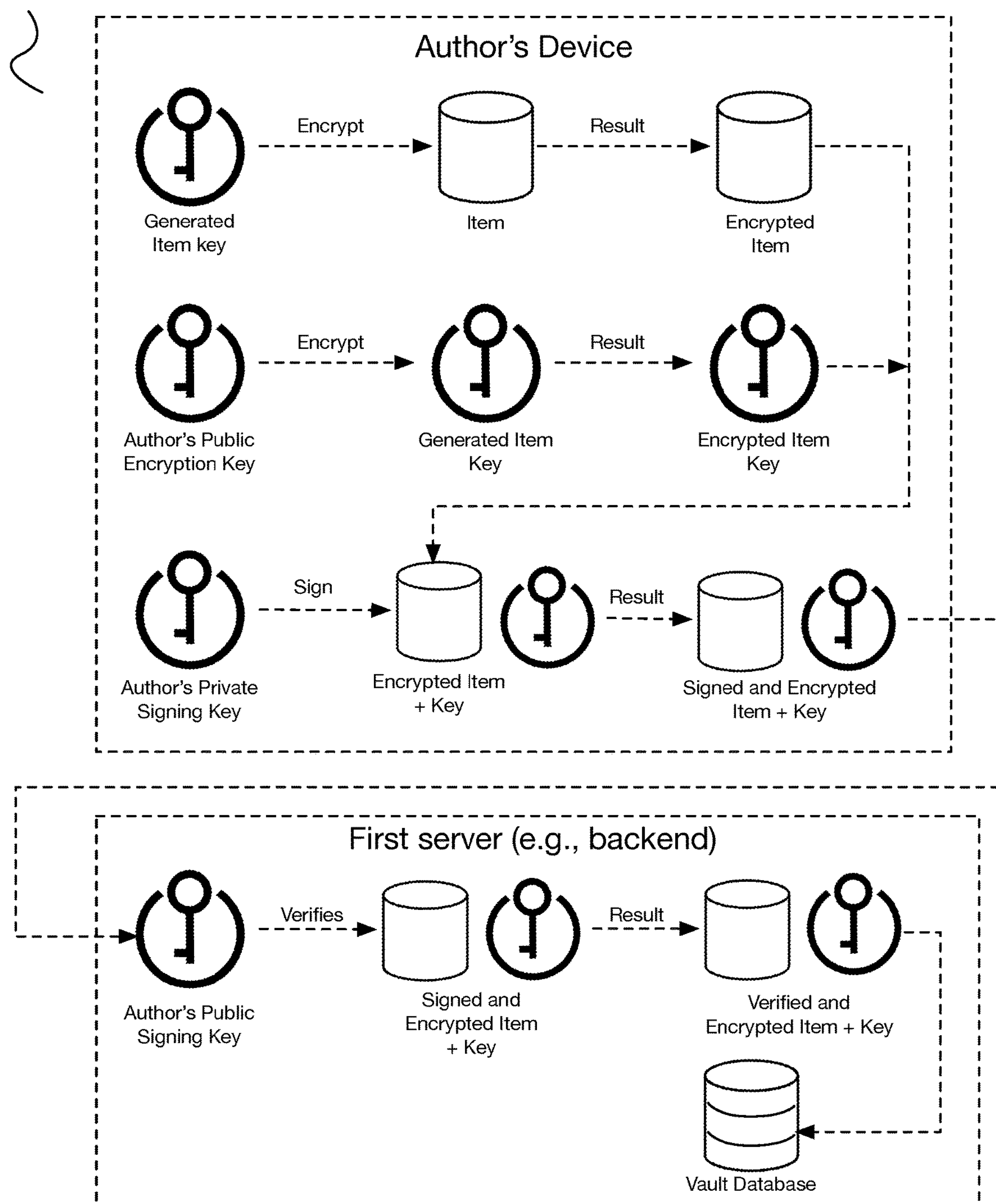
FIG. 5 depicts a schematic variation of encrypting items.

In preferred variations (e.g., as shown in FIG. 5), S230 includes: generating a unique item key on a device; encrypting the item with the item key; encrypting the item key with the author's public encryption key; signing the encrypted data with the user's (e.g., author's) private signing key (e.g., to create an audit log with cryptographic guarantees); sending the signed and encrypted items along with their item keys to the server (e.g., via the client library); and at the server, verifying the signature, wherein if the signature is valid, the encrypted data persists and an entry is added to an audit log. Additionally or alternatively, encrypting items (e.g., of the author) can include any other suitable processes or combination of processes including any suitable keys.

In an alternative variation, for instance, the items are encrypted in absence of encrypting the item key.

4.4 Method: Sharing Items S240

The method 200 preferably includes sharing items S240, which functions to securely share data among and/or between any or all of: users, supplementary systems, servers, and/or any other entities.

S240 is preferably performed after S230 (e.g., with encrypted items), but can additionally or alternatively be performed in parallel with S230, after any other processes of the method, multiple times during the method 200, in parallel with any other processes of the method 200, in response to a trigger (e.g., request of the item by the user, request to share an item by an author, updates to the users in groups, etc.), and/or any other times Additionally or alternatively, the method 200 can be performed in absence of S240.

Sharing an item preferably includes receiving (e.g., from an author) and/or determining (e.g., based on a set of groups) a set of recipients associated with the item. In preferred variations (e.g., as described above), the public encryption keys of these recipients are then used to encrypt an item key of the associated item. Any or all of these recipients can optionally be selected by and/or designated by the author. In some variations, for instance, an author can specify a particular coach and/or supervisor and/or clinician and/or member to whom he or she desires the item and/or a copy of the item to be viewed by and/or otherwise accessible to. These can include any or all of: all users (e.g., wherein the author has full freedom to select a recipient and/or system), a subset of users (e.g., only those assigned to a predetermined set of groups associated with the user), any other users, and/or any combination. Additionally or alternatively, any or all of the recipients can be automatically determined, such as based on any or all of: a predetermined set of recipients (e.g., as specified by a set of groups as described above), a dynamically determined set of recipients (e.g., based on a dynamically updated set of groups, with a trained model and/or algorithm, etc.), a set of systems and/or entities (e.g., platform billing systems, platform compliant systems, etc.), any combination, and/or any other recipients.

Sharing an item preferably includes: encrypting the plaintext item encryption key with the recipient's public encryption key and uploading the newly encrypted key to the server (e.g., as described above in S230). Additionally or alternatively, sharing an item can include any other suitable processes.

Figure 6:
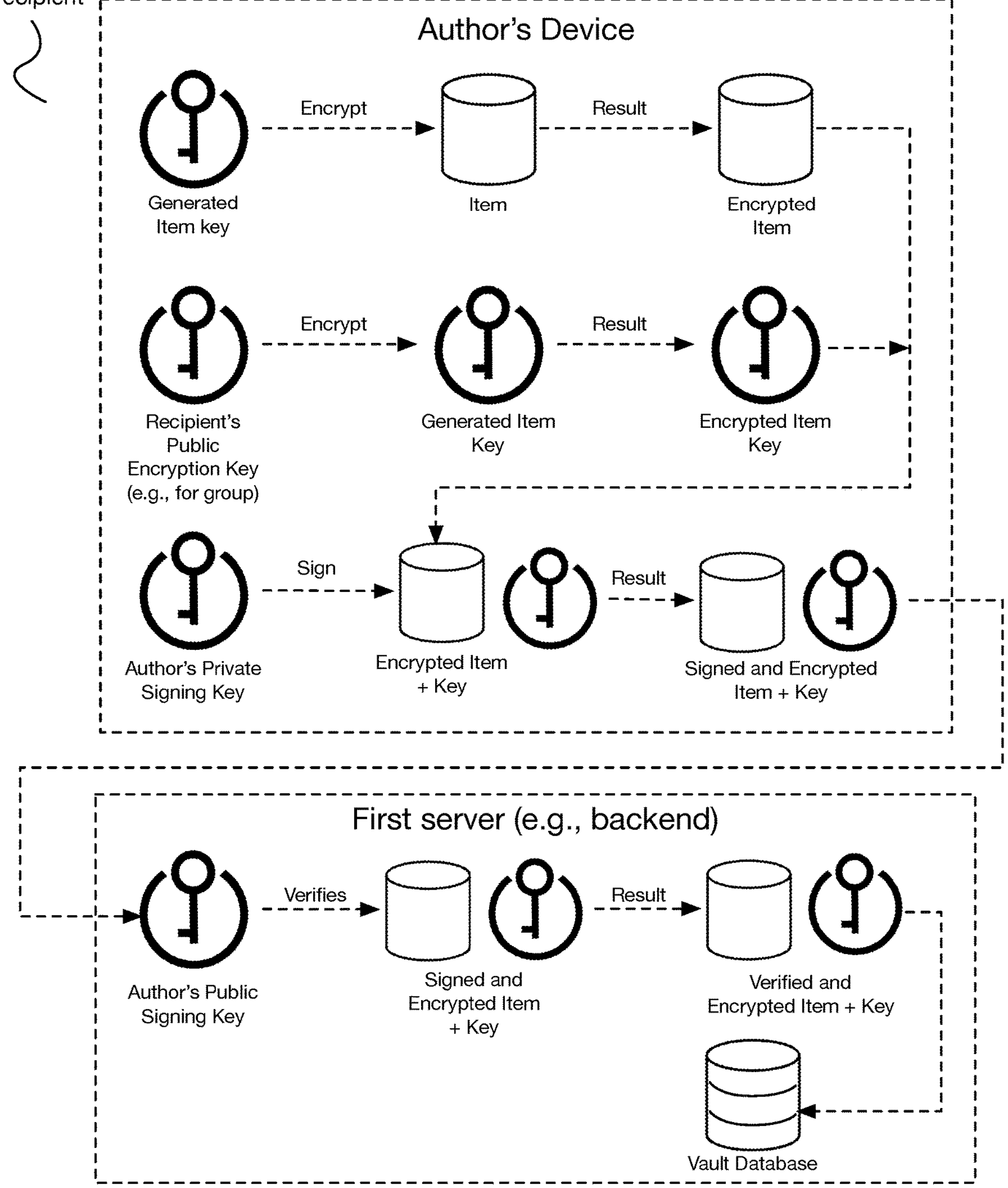
FIG. 6 depicts a schematic variation of encrypting items to be accessible to a recipient (e.g., group, particular user, etc.).
Figure 7:
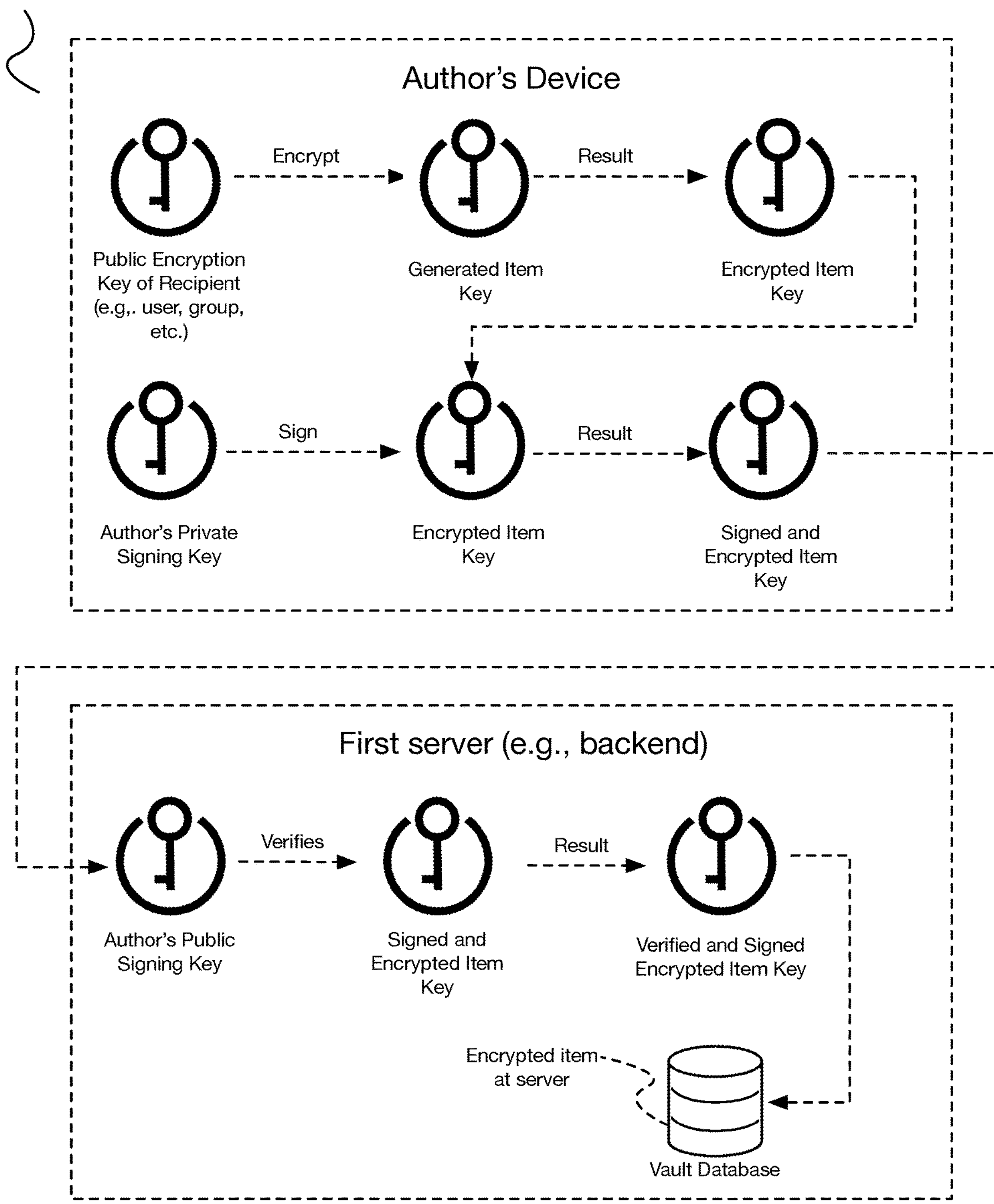
FIG. 7 depicts a schematic variation of sharing items.

In preferred variations of S240 (e.g., as shown in FIG. 7), S240 includes, for an item (e.g., of a user, of an author, of a supervisor, of a supplementary system, at a device, etc.): encrypting the relevant item key with the recipient's public key; signing the encrypted item key with the author's private signing key; sending the encrypted item key to the server; and, at the server, verifying the signature, wherein if the signature is valid, the encrypted item key persists and an entry is optionally added to the audit log. The verified and signed encrypted item key can then be attributed to (e.g., assigned to) an associated item and/or a copy of the associated item (e.g., a single copy of the item stored at the vault database, a copy of the item relative to the item uploaded by the author, etc.), and/or the process shown in FIG. 7 can be performed for a particular item (e.g., as shown in FIG. 6). Additionally or alternatively, encrypting items of the author can include any other suitable processes or combination of processes including any suitable keys.

In a first variation, items are shared with a set of recipients specifically designated by the author, wherein the item key associated with the item (and/or a copy or copies of the item) is encrypted with the public encryption keys of the set of recipients. In a specific example, a copy of the item is made for each of these recipients, wherein each copy's item key is encrypted with a public encryption key of one of these recipients. In additional or alternative specific examples, an item is encrypted with all of the public encryption keys of the recipients.

In a second variation (e.g., as shown in FIG. 6), additional or alternative to the first, each item key (and/or item keys of its copy/copies) is encrypted (e.g., automatically, upon designation by the author, etc.) with a public encryption key associated with a group assigned to the author, such that all users in the group can access the item. Additionally or alternatively, the key can be encrypted with the public encryption key(s) of users within the group.

In a third variation, additional or alternative to any or all of those described above, any other entities and/or groups associated with the program/platform (e.g., clinical billing entity, report generation entity, etc.) can be automatically designated (e.g., and/their associated public encryption keys used to encrypt the item keys). This is preferably automatically handled at the API layers of client applications, but can additionally or alternatively be manually designated and/or otherwise handled.

Additionally or alternatively, S240 can include any other suitable processes.

4.5 Method: Reading Items S250

The method 200 can optionally include reading items S250, which functions to enable users and/or other systems/entities (e.g., 3rd party systems, 3rd party client applications, etc.) to be able to access items from the first server. The items can include any or all of: items that the user or entity created, items that another user or entity created (e.g., which the user and/or entity has access/permissions to, which have been shared with the user in S240, etc.), items available to all users and/or entities, and/or any other items.

Enabling a user and/or entity to read items (equivalently referred to herein as access items) is preferably performed in accordance with a set of permissions and/or access rules associated with the user and/or entity, which functions to prevent, for instance, any or all of the users and/or entities from being able to access all of the items in the first server. The set of permissions preferably includes permissions set on a per-item basis. In some variations, for instance, each item is associated with a particular set of users and/or entities which are permitted to access the item. In specific examples involving users (e.g., coaches), for instance, a user can access: items which he or she created, items which were created by another user who is part of one or more of the set of groups (e.g., coaching groups) associated with the user, and items which are/were specifically shared with the user (e.g., as described in S240). Additionally or alternatively, the user can access a subset of these items, additional items, and/or any other items.

Further additionally or alternatively, one or more users and/or entities can have access to all items in the first server (e.g., with temporal delays between access to subsets of items, all at once, etc.), and/or permissions/access to items can be otherwise designated and/or enforced.

Further additionally or alternatively, access to any or all of the items can be limited to any or all of the users in accordance with any or all of: one or more thresholds, a set of decision trees (e.g., configured to indicate irregular activity), one or more models and/or algorithms (e.g., trained models configured to detect irregular activity), and/or any other tools. The limits of this access can be: predetermined (e.g., based on the thresholds, based on programmed rules, based on a set of decision trees, etc.), dynamically determined (e.g., based on trained models), and/or any combination.

In preferred variations, for instance, the method 200 includes restricting users and/or supplementary systems from accessing all items and/or other information (e.g., keys, keypairs, etc.). In a first set of variations, for instance, some or all users (e.g., supervisors, coaches, clinicians, all users, etc.) are restricted from having access to every item (e.g., of all items in the first server, of all items in the first server that they have access to, of all items in the first server that they have access to based on their group assignments, etc.) at once.

In some examples, users (e.g., supervisors, coaches, clinicians, etc.) are given credentials to access ("check out") at most a predetermined number of items (e.g., 1, 2, 3, 4, 5, between 1 and 10, greater than 10, etc.) and/or a predetermined subset of items (e.g., only items from a single group, only items from all of their groups, etc.) at a time. Additionally or alternatively, a user can be suspended (e.g., temporarily, for a predetermined amount of time, until the issue is resolved, until the user successfully logs back in, etc.) from accessing data in an event that suspicious activity (e.g., attempt to access more than the predetermined number of items, attempt to access greater than a threshold number of items, attempt to access a large number of items in a short time period, activity which points to the user being a robot/bot, etc.) occurs.

In first set of specific examples, each user of the set of users and/or a subset of the set of users (e.g., coaches, supervisors, clinicians, etc.) is associated with a predetermined number of groups (e.g., 2 groups as described above, more than 2 groups, etc.), wherein in an event that the user is requesting access to information associated with his or her groups (e.g., as opposed to information specifically shared with the user), the user can only read items from a single group at a time (e.g., in a single request/call/query). Additionally or alternatively, any or all of the users (e.g., coaches, clinicians, supervisors, etc.) can only access items associated with a single member at a time, only access items created by a single author at a time, can only access items below a predetermined number at a time, and/or the user can otherwise have other access. Further additionally or alternatively, any or all of the users can access items from multiple groups at a time (e.g., from any or all of their assigned groups), can have unlimited access to items, and/or the users can otherwise interact with items.

S250 can additionally or alternatively include triggering one or more alarms and/or alerts (e.g., at the first server, at a monitoring entity of the first server, etc.) in response to detecting that a user is trying to access a large number of items in a short time period, which can indicate, for instance, the user's account (e.g., set of master keys) has been compromised and a machine is attempting to access large amounts of data. This is preferably detected based on the audit log, but can additionally or alternatively be otherwise detected.

Reading items preferably includes receiving (e.g., retrieving, fetching, etc.), at a user device of the recipient (e.g., via an API layer and/or client application), a set of keys from the first server along with the encrypted item. The set of keys preferably includes encrypted keys, which the recipient then decrypts at the user device (e.g., with his or her master key(s)), but can additionally or alternatively include decrypted keys, unencrypted (e.g., plaintext) keys, and/or any other keys. In preferred variations, reading items includes retrieving, at the first server, the encrypted private encryption key of the recipient, the encrypted item key of the item, and the encrypted item. Additionally or alternatively, any other information can be retrieved from the first server and/or any other servers, such as, but not limited to, any or all of: encrypted keys of the author, decrypted and/or unencrypted keys, and/or any other information.

Reading items further preferably includes validating a signature associated with the item, which functions to verify that the item has not been tampered with (e.g., since being uploaded by the author, when uploaded by the author, etc.) and/or can verify any other feature(s) associated with the item. This is preferably performed with a public signing key of the author (e.g., which is stored at the first server), but can additionally or alternatively be performed with any other key(s) and/or processes. Additionally or alternatively, items can be uploaded and/or read in absence of signing keys and/or a validation process.

Reading items further preferably includes decrypting the encrypted keys and encrypted item retrieved from the first server. This is preferably performed after validating the signature, but can additionally or alternatively be performed prior to validating the signature, in absence of validating a signature, and/or at any other times. In preferred variations, decrypting the information includes: decrypting the encrypted private encryption key with the author's master key (e.g., randomly generated key held by the user and not sent to the first server); decrypting the item key with the decrypted private encryption key; and decrypting the items with the decrypted item key. Additionally or alternatively, the item can be otherwise accessed.

In variations in which the user is accessing an item associated with a group of the user, the encrypted private encryption key can instead and/or additionally include an encrypted private encryption key of the group (e.g., as described above). This encrypted private encryption key of the group is preferably able to be decrypted by the user's private encryption key (e.g., as retrieved with the recipient's master key), but can additionally or alternatively require a different private encryption key, a different master key, and/or can be otherwise decrypted.

In additional or alternative variations, when a recipient is accessing an item that was shared with a group to which the recipient belongs, the encryption key needed to decrypt the item would have been encrypted with the recipient's public encryption key. As such, the recipient can then decrypt the encryption key for the item with his or her private encryption key.

Figure 8:
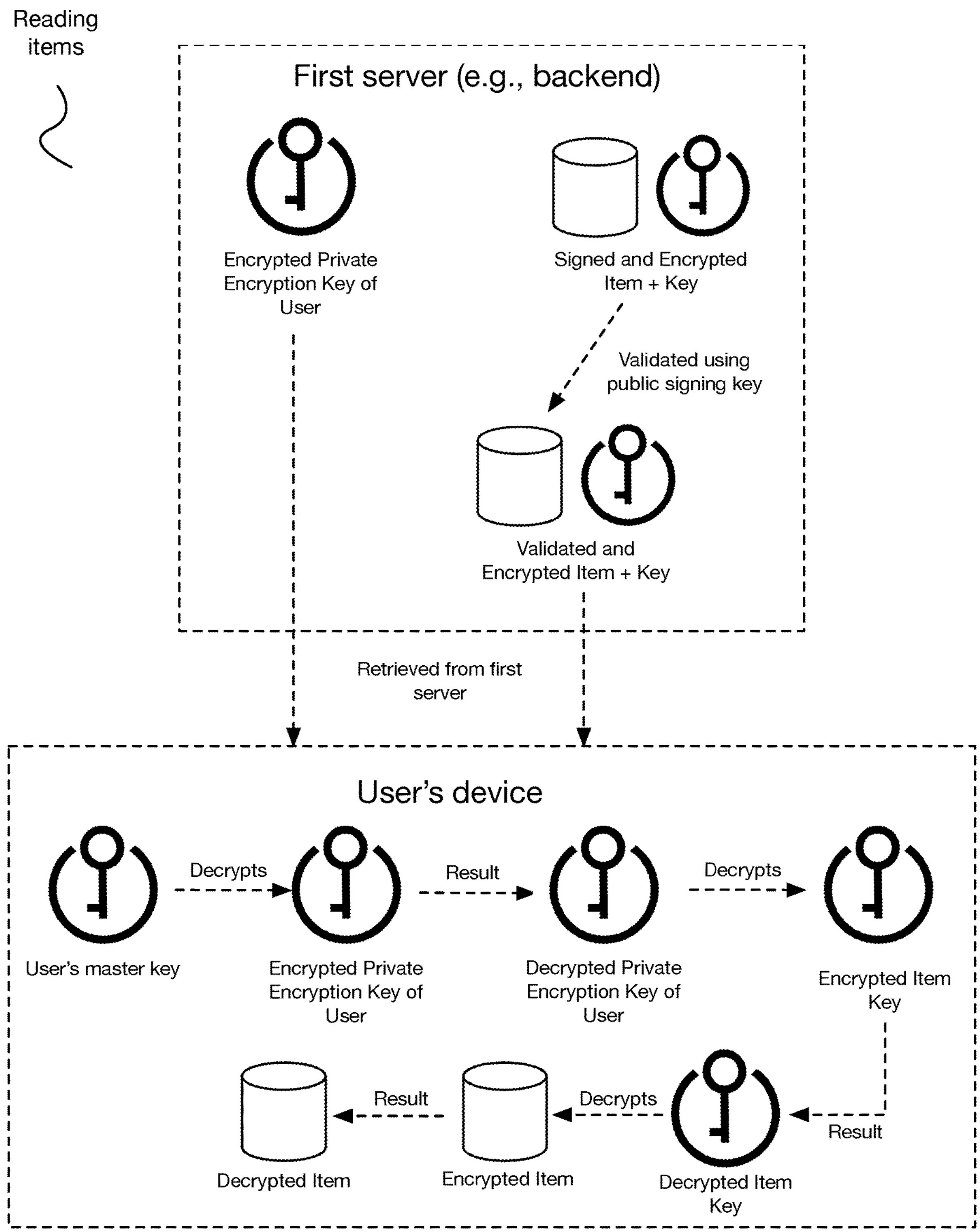
FIG. 8 depicts a schematic variation of reading items.

In a first variation (e.g., as shown in FIG. 8), reading items (e.g., owned items, shared items, etc.) (e.g., by a user, by an author, by a supervisor, by a supplementary system, at a device, etc.) by the recipient includes any or all of: fetching the encrypted private encryption key of the recipient, the encrypted item key, and the encrypted item from the first server; validating signature(s) of the encrypted item and encrypted item key using a public signing key of the author; decrypting the encrypted private encryption key of the recipient with the recipient's master key, which is preferably a randomly generated key held by the recipient and not sent to the server; decrypting the item key with the decrypted private encryption key; and decrypting the items with their item keys. Additionally or alternatively, reading items can include any other suitable processes or combination of processes including any suitable keys.

In a second variation, reading items by the recipient includes any or all of: fetching the encrypted private encryption key of a group associated with the recipient, wherein the author of the item is from the group, the encrypted item key, and the encrypted item from the first server; validating signature(s) of the encrypted item and encrypted item key using a public signing key of the author; decrypting the encrypted private encryption key of the group with the recipient's master key, which is preferably a randomly generated key held by the recipient and not sent to the server; decrypting the item key with the decrypted private encryption key; and decrypting the items with their item keys. Additionally or alternatively, reading items can include any other suitable processes or combination of processes including any suitable keys.

Additionally or alternatively, S250 can include any other suitable processes.

4.6 Method: Recording an Audit Log S260

The method 200 can optionally include recording an audit log, which functions to keep a record of and optionally set triggers based on activity of any or all of the users and supplementary systems with respect to items at the server.

An entry into the audit log is preferably created automatically in response to any or all of the processes described above, such as, but not limited to, any or all of: an author creating an item, an author editing an item, an author uploading an item, an author sharing an item, a recipient reading an item, and/or any other actions (e.g., a user and/or supplementary system registering with the first server. Additionally or alternatively, entries to the audit log can be performed in response to any other processes, a subset of these processes, and/or any combination.

Entries to the audit log can include any or all of: a time (e.g., timestamp) at which the action was taken, which user and/or supplementary system performed the action, the particular item (e.g., item ID) involved in the action, what the action was (e.g., uploading item, reading item, sharing item, etc.), and/or any other information.

The audit log is preferably not editable, but can additionally or alternatively be selectively editable (e.g., by a subset of users, for a subset of items, etc.), and/or any combination.

The audit log is preferably only viewable by a set of administrators and/or any other monitoring entities associated with the first server and/or platform/program, but can additionally or alternatively be accessible to any or all of the users and/or supplementary systems, and/or to any other entities (e.g., other servers).

Any or all of the audit log can optionally be created and/or verified using signing keys associated with the users and/or supplementary systems, such as any or all of the signing keys and/or signing keypairs. In preferred variations, for instance, each user has a signing public-private keypair, which functions to provide authentication of the user as well as record the actions of the user with respect to viewing and/or creating and/or sharing and/or receiving items in an audit log.

In a preferred set of variations, entries to the audit log are automatically added in response to any or all of the processes described above.

In additional or alternative variations, entries to the audit log can be manually added and/or otherwise added.

5. Variations

In a first variation of the system 100, the system includes: a first server configured to store a set of data items, wherein each of the set of data items is a portion of a larger data piece, and wherein each of the set of data items is encrypted with an item key, and wherein each item key is encrypted with a public encryption key associated with a user of the set of users; a first subset of keys stored at the first server; a second subset of keys stored and/or accessible at a user device of a user; an audit log associated with the set of users' actions of the set of data items, wherein entries to the audit log are automatically recorded and triggered based on the users' actions; optionally a second server, wherein the second server stores a decrypted duplicate of each of the set of data items; optionally additionally databases including processed versions of the decrypted duplicate items; and/or any other components.

In a first specific example, the 1$^{st}$ subset of keys includes an encrypted public-private encryption keypair for each user and/or group and/or supplementary system (e.g., wherein the public-private encryption keypair is encrypted with a master encryption key of the user), an unencrypted (e.g., plaintext) public encryption key for each user and/or group and/or supplementary system; and an unencrypted (e.g., plaintext) public signing key.

Additionally or alternatively, the 1$^{st}$ subset of keys can include any other keys.

In a second specific example, additional or alternative to the first, the system includes a second server, wherein information is communicated from the first server to the second server but not from the second server to the first server, and wherein at least a portion (e.g., majority, greater than 50%, greater than 70%, greater than 90%, greater than 95%, etc.) if not all of the users are not provided with access to the second server.

Additionally or alternatively, the system 100 can include any other components or combination of components.

In a first variation, the method 200 can include any or all of: registering each user and/or supplementary system with the server; registering devices of the user with the server; creating items; encrypting items and at least a portion of the keys and keypairs; sharing items; reading items; and recording entries in an audit log.

In a first specific example of encrypting items and uploading them to the first server, the method can include any or all of: at a user device associated with a user, encrypting an item (e.g., generated at a client application corresponding to the digital health platform, otherwise generated at the user device, generated offboard the user device, etc.) with an item key to form an encrypted item; encrypting the item key with a first public encryption key, the first public encryption key associated with the first user, to form an encrypted item key; signing the encrypted item and the encrypted item key with a first private signing key associated with the first user to form a signed encrypted item and a signed encrypted item key; transmitting the signed encrypted item and the signed encrypted item key to a remote server; uploading the encrypted item with encrypted item key to the remote server; and at the remote server, verifying the signed encrypted item and the signed encrypted item key with a public signing key of the user, wherein the public signing key of the user is stored at the remote server; and recording an entry in an audit log based on verifying the signed encrypted item and the signed encrypted item key.

Additionally or alternatively, the method can include reading items from the first server, which preferably includes: fetching the encrypted private encryption key of the recipient, the encrypted item key, and the encrypted item from the first server; validating signature(s) of the encrypted item and encrypted item key using a public signing key of the author; decrypting the encrypted private encryption key of the recipient with the recipient's master key, which is preferably a randomly generated key held by the recipient and not sent to the server; decrypting the item key with the decrypted private encryption key; and decrypting the items with their item keys. Additionally or alternatively, reading items can include any other suitable processes or combination of processes including any suitable keys.

Additionally or alternatively, the method can include sharing items with a set of recipients specifically designated by the author, wherein the item key associated with the item (and/or a copy or copies of the item) is encrypted with the public encryption keys of the set of recipients. In a specific example, a copy of the item is made for each of these recipients, wherein each copy's item key is encrypted with a public encryption key of one of these recipients. In additional or alternative specific examples, an item is encrypted with all of the public encryption keys of the recipients.

Additionally or alternatively, each item key (and/or item keys of its copy/copies) can be encrypted (e.g., automatically, upon designation by the author, etc.) with a public encryption key associated with a group assigned to the author, such that all users in the group can access the item. Further additionally or alternatively, the key can be encrypted with the public encryption key(s) of users within the group.

Additionally or alternatively, the method 200 can include any other suitable processes or combination of processes.

Although omitted for conciseness, the preferred embodiments include every combination and permutation of the various system components and the various method processes, wherein the method processes can be performed in any suitable order, sequentially or concurrently.

As a person skilled in the art will recognize from the previous detailed description and from the figures and claims, modifications and changes can be made to the preferred embodiments of the invention without departing from the scope of this invention defined in the following claims.

We claim:

1. A method for managing information associated with a set of users of a digital program, the method comprising:
- at a user device associated with a user of the set of users:
  - receiving a set of data items;
  - performing a set of encryption processes on the set of data items to produce a set of encrypted outputs, the set of encrypted outputs comprising a set of encrypted data items, wherein producing the set of encrypted outputs comprises, for each of the set of data items:
    - encrypting the data item with an item key;
    - encrypting the item key with a public encryption key associated with the user to produce an encrypted item key; and
    - signing the encrypted item and the encrypted item key with a private signing key associated with the user;
  - transmitting the set of encrypted outputs to a first server;
- producing a decrypted duplicate of each of the set of data items, to produce a set of decrypted duplicate data items;
- uploading the set of decrypted duplicate data items to a second server; and
- producing data in a set of databases, the set of databases absent of communication with the first server, wherein at least a portion of the set of databases is in communication with the second server, wherein producing data in the set of databases comprises:
  - producing data in a first database of the set of databases through at least one of: a de-identification process and an anonymization process; and
  - producing data in a second database through a sampling process.

2. The method of claim 1, wherein the user is unable to access the set of decrypted duplicate data items in the second server.

3. The method of claim 1, wherein the sampling process comprises sampling a portion of data from the first database for inclusion in the second database.

4. The method of claim 1, further comprising developing an initial set of models utilized in the digital program based on the data in the second database.

5. The method of claim 4, further comprising training the initial set of models based on the data in the first database to produce a trained set of models.

6. The method of claim 5, further comprising producing a set of outputs with the trained set of models and based on the set of data items, wherein the set of outputs is provided at the user device.

7. A system for managing information associated with a set of users of a digital program, the system comprising:
- a first data storage subsystem, wherein the first data storage subsystem comprises:
  - a set of encrypted data items produced based on a set of data items received from a set of applications associated with the set of users;
  - an encrypted public-private encryption keypair; and
  - a set of unencrypted keys comprising an unencrypted public encryption key and an encrypted private encryption key;
- a second data storage subsystem, wherein the second data storage subsystem comprises:
  - a decrypted duplicate of each of the set of data items;
- a third data storage subsystem in communication with the second storage subsystem and absent of communication with the first data storage subsystem,
- wherein the third data storage subsystem comprises:
  - a first set of data, wherein the first set of data is produced with at least one of a de-identification process and an anonymization process;
- a fourth data storage subsystem absent of communication with the first data storage subsystem, wherein the fourth data storage subsystem comprises:
  - a second set of data, wherein the second set of data is produced with a sampling process; and
- a set of computing devices comprising a set of servers selectively in communication with the first, second, third, and fourth data storage subsystems.

8. The system of claim 7, wherein the first data storage subsystem further comprises an audit log associated with a set of actions involving the set of data items.

9. The system of claim 7, wherein no user of the set of users is provided with access to the second data storage subsystem.

10. The system of claim 9, wherein a user of the set of users can access a data item of the encrypted set of data items in response to satisfaction of a set of satisfaction criteria, the set of satisfaction criteria comprising at least one of:
- a public encryption key encrypting an item key, wherein the item key encrypts the data item, is a public encryption key of the user; and
- a public encryption key encrypting the item key is a public encryption key of a group, wherein the user is assigned to the group.

11. The system of claim 7, wherein the first data storage subsystem is in communication with a computing subsystem, wherein the computing subsystem implements a set of trained models to produce a set of outputs at the set of applications based on the set of data items.

12. The system of claim 11, wherein the set of trained models is trained based on the first set of data.

13. The system of claim 12, wherein the set of trained models is refined relative to an initial set of models, the initial set of models determined based on the second set of data.

14. The system of claim 13, wherein a second set of users is provided access to the fourth storage subsystem for development of the initial set of models, the second set of users separate and distinct from the first set of users.

* * * * *